United States Patent
Kim et al.

(10) Patent No.: US 9,499,523 B2
(45) Date of Patent: Nov. 22, 2016

(54) PHOSPHATIDYLINOSITOL 3-KINASE INHIBITORS

(71) Applicant: Gilead Sciences, Inc., Foster City, CA (US)

(72) Inventors: Musong Kim, Bothell, WA (US); Stephane Perreault, Brier, WA (US); Suet Chung Yeung, Redmond, WA (US)

(73) Assignee: GILEAD SCIENCES, INC., Foster City, CA (US)

( * ) Notice: Subject to any disclaimer, the term of this patent is extended or adjusted under 35 U.S.C. 154(b) by 0 days.

(21) Appl. No.: 14/736,025

(22) Filed: Jun. 10, 2015

(65) Prior Publication Data

US 2015/0361071 A1    Dec. 17, 2015

Related U.S. Application Data

(60) Provisional application No. 62/011,905, filed on Jun. 13, 2014.

(51) Int. Cl.
| | | |
|---|---|---|
| C07D 403/14 | (2006.01) | |
| C07D 471/04 | (2006.01) | |
| C07D 491/048 | (2006.01) | |
| C07D 487/04 | (2006.01) | |

(52) U.S. Cl.
CPC ............ C07D 403/14 (2013.01); C07D 471/04 (2013.01); C07D 487/04 (2013.01); C07D 491/048 (2013.01)

(58) Field of Classification Search
CPC .................................................. C07D 487/03
See application file for complete search history.

(56) References Cited

U.S. PATENT DOCUMENTS

| | | |
|---|---|---|
| 6,800,620 B2 | 10/2004 | Sadhu et al. |
| 8,435,988 B2 | 5/2013 | Qu et al. |
| 8,673,906 B2 | 3/2014 | Barlaam et al. |
| 2013/0274253 A1 | 10/2013 | Brollo et al. |
| 2015/0361054 A1 | 12/2015 | Cai et al. |
| 2015/0361068 A1 | 12/2015 | Cai et al. |
| 2015/0361070 A1 | 12/2015 | Evarts et al. |
| 2015/0361095 A1 | 12/2015 | Du et al. |

FOREIGN PATENT DOCUMENTS

| | | |
|---|---|---|
| WO | WO-2015/191754 A2 | 12/2015 |
| WO | WO-2015191726 A1 | 12/2015 |
| WO | WO-2015191743 A1 | 12/2015 |
| WO | WO-2015191745 A1 | 12/2015 |
| WO | WO-2015191752 A1 | 12/2015 |

OTHER PUBLICATIONS

McMahon et al (2000).*
Pinedo et al (2000).*
Engelman, et al. (2009), "Targeting PI3K Signalling in Cancer: Opportunities, Challenges and Limitations", Nat. Rev. Cancer, 9: 550-562.
Foster, A. (1984) "Deuterium Isotope Effects in Studies of Drug Metabolism", Trends Pharmacol. Sci., 5(12):524-527.
Hiles, et at. (1992), "Phosphatidylinositol 3-Kinase: Structure and Expression of the 110 kd Catalytic Subunit", Cell, 70; 419-429.
Otsu, et al. (1991) "Characterization of Two 85kd Proteins that Associate with Receptor tyrosine Kinases, Middle-T/pp60c-src Complexes, and PI3-Kinase", 65:91-104.
Panayotou, G. et al. (1992), "Phosphatodyl-inositol 3-Kinase: a Key Enzyme in Diverse Signalling Processes", Trends in Cell Biology, 2: 358-360.
Rameh, L. et al., (1999), "The Role of Phosphoinositide 3-Kinase Lipid Products in Cell Function" The Journal of Biological Chemistry 274(13): 8347-8350.
Int'l Search Report dated Dec. 29, 2015 for PCT/US2015/035161.
Int'l Search Report dated Dec. 17, 2015 for PCT/US2015/035126.
Int'l Search Report dated Dec. 17, 2015 for PCT/2015/035157.
Int'l Search Report dated Dec. 17, 2015 for PCT/US2015/035147.
Int'l Search Report dated Dec. 17, 2015 for PCT/US2015/035145.
Written Opinion dated Dec. 29, 2015 for PCT/US2015/035161.
Written Opinion dated Dec. 17, 2015 for PCT/US2015/035157.
Written Opinion dated Dec. 17, 2015 for PCT/US2015/035126.
Written Opinion dated Dec. 17, 2015 for PCT/US2015/035145.
Written Opinion dated Dec. 17, 2015 for PCT/US2015/035147.

* cited by examiner

Primary Examiner — Paul V Ward
(74) Attorney, Agent, or Firm — Roy Issac

(57) ABSTRACT

The present application provides the compounds of formula (J),

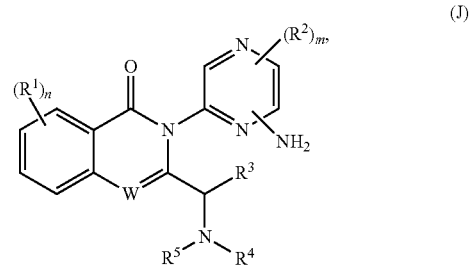

or pharmaceutically acceptable salts, isomers, tautomer, or a mixture thereof, wherein n, m, $R^1$, $R^2$, $R^3$, $R^4$, and $R^5$ are described herein. The compounds are inhibitors to the activities of phosphatidylinositol 3-kinase (PI3K) and are useful for treating conditions mediated by one or more PI3K isoforms. The present application further provides pharmaceutical compositions that include a compound of formula (I), or pharmaceutically acceptable salts, isomers, tautomer, or mixture thereof, and methods of using these compounds and compositions for treating conditions mediated by one or more PI3K isoforms.

32 Claims, No Drawings

PHOSPHATIDYLINOSITOL 3-KINASE INHIBITORS

This application claims the benefit and the priority of U.S. provisional patent application Ser. No. 62/011,905, filed Jun. 13, 2014, the disclosure is incorporated herein by reference in the entirety.

FIELD

The present application relates to novel compounds that selectively inhibit the activities of PI3K isoforms and their uses in therapeutic treatments.

BACKGROUND

Cell signaling via 3'-phosphorylated phosphoinositides has been implicated in a variety of cellular processes, e.g., malignant transformation, growth factor signaling, inflammation, and immunity (Rameh et al., *J. Biol. Chem.*, 274: 8347-8350, 1999). Phosphatidylinositol 3-kinase (PI 3-kinase or PI3K) is responsible for generating these phosphorylated signaling products. PI3K was initially identified as a protein associated with viral oncoproteins and growth factor receptor tyrosine kinases that phosphorylate phosphatidylinositol (PI) and its phosphorylated derivatives at the 3'-hydroxyl of the inositol ring (Panayotou et al., *Trends Cell Biol.*, 2:358-60, 1992).

Three classes of the PI 3-kinase (PI3K) are proposed based on the substrate specificities. Class I PI3Ks phosphorylate phosphatidylinositol (PI), phosphatidylinositol-4-phosphate, and phosphatidylinositol-4,5-biphosphate (PIP$_2$) to produce phosphatidylinositol-3-phosphate (PIP), phosphatidylinositol-3,4-biphosphate, and phosphatidylinositol-3,4,5-triphosphate, respectively. Also, Class II PI3Ks phosphorylate PI and phosphatidylinositol-4-phosphate, and Class III PI3Ks phosphorylate PI.

The initial purification and molecular cloning of PI 3-kinase revealed that it was a heterodimer consisting of p85 and p110 subunits (Otsu et al., *Cell*, 65:91-104, 1991; Hiles et al., *Cell*, 70:419-29, 1992). Later, four distinct Class I PI3Ks were identified and designated as PI3K α, β, δ, and γ isoforms. Each isoform consists of a distinct 110 kDa catalytic subunit and a regulatory subunit. The catalytic subunits of PI3K α, β, and δ (i.e., p110α, p110β, and p110δ, respectively) interacts, individually, with the same regulatory subunit p85, whereas the catalytic subunit of PI3K γ (p110γ) interacts with a distinct regulatory subunit p101.

Studies have also showed that each PI3K isoform has distinct expression pattern. For example, PIK3CA which encodes PI3Kα is frequently mutated in human cancers (Engelman, *Nat. Rev. Cancer*, 9: 550-562, 2009). Also, PI3K is generally expressed in hematopoietic cells. Moreover, PI3K isoforms are shown to be associated with proliferation or survival signaling in cancers, inflammatory, or autoimmune diseases. As each PI3K isoform has different biological function. PI3K isoforms are potential targets to treat cancer or disorder (U.S. Pat. Nos. 6,800,620; 8,435,988; 8,673.906; US Patent Application Publication No. US2013/0274253).

Therefore, there is a need for developing therapeutic agents that inhibit PI3K isoforms to treat diseases, disorders, or conditions that are mediated by PI3K.

SUMMARY

The present application provides novel compounds that are inhibitors of PI3K isoforms. The application also provides compositions, including pharmaceutical compositions, kits that include the compounds, and methods of using and making the compounds. The compounds provided herein are useful in treating diseases, disorders, or conditions that are mediated by PI3K isoforms. The application also provides compounds for use in therapy. The application further provides compounds for use in a method of treating a disease, disorder, or condition that is mediated by PI3K isoforms. Moreover, the application provides uses of the compounds in the manufacture of a medicament for the treatment of a disease, disorder or condition that is mediated by PI3K isoforms.

The applications provides the compounds having the structure of formula (I):

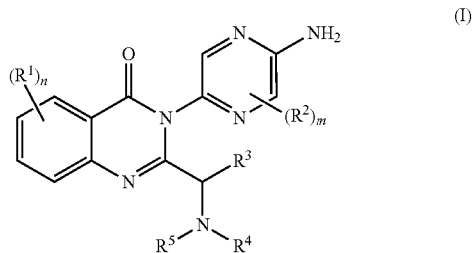

wherein:

n is 1, 2, or 3;

m is 0 or 1;

each $R^1$ is independently selected from halo, cyano, optionally substituted $C_{1-6}$ alkyl, optionally substituted $C_{1-6}$ haloalkyl, optionally substituted $C_{1-6}$ alkoxy, optionally substituted sulfonyl, optionally substituted $C_{3-8}$ aryl, optionally substituted $C_{3-8}$ heteroaryl, optionally substituted $C_{3-8}$ cycloalkyl, and optionally substituted $C_{3-8}$ heterocycloalkyl;

each $R^2$ is independently selected from halo and optionally substituted $C_{1-6}$ alkyl;

$R^3$ is hydrogen, optionally substituted $C_{1-6}$ alkyl, optionally substituted $C_{6-10}$ aryl, or optionally substituted $C_{3-8}$ cycloalkyl;

$R^4$ is a six- to twelve-membered heteroaryl having at least one aromatic group and at least two heteroatoms, wherein the heteroatoms are selected from N, O, or S, wherein the heteroaryl is optionally substituted with one, two, or three members independently selected from halo, cyano, optionally substituted haloalkyl, optionally substituted $C_{1-6}$ alkyl, and —NH$_2$; and $R^5$ is hydrogen or optionally substituted $C_{1-6}$ alkyl, wherein $R^5$ and $R^3$ together with the atoms to which they are attached optionally form a four- or eight-membered heterocyclic ring; or a pharmaceutically acceptable salt, isomer, or a mixture thereof.

The application also provides the compound having the structure of formula (I), wherein:

n is 1 or 2;

m is 0 or 1;

each $R^1$ is independently selected from halo, $C_{1-6}$ alkyl, and $C_{1-6}$ haloalkyl;

each $R^2$ is independently $C_{1-6}$ alkyl:

$R^3$ is hydrogen, $C_{1-6}$ alkyl, or $C_{3-8}$ cycloalkyl;

$R^4$ is a six- to twelve-membered heteroaryl having at least one aromatic ring and at least two nitrogen atoms, wherein the heteroaryl is optionally substituted with one, two, or three members independently selected from halo, cyano, —NH$_2$, $C_{1-6}$ haloalkyl, and $C_{1-6}$ alkyl; and $R^5$ is hydrogen, methyl, ethyl, or propyl, or $R^5$ and $R^3$ together with the atoms to which they are attached optionally form a five-membered heterocyclic ring;

or a pharmaceutically acceptable salt, isomer, or a mixture thereof.

In one aspect, the compound of the present application having the structure of formula (I), wherein each $R^1$ is independently selected from chloro, bromo, fluoro, methyl, ethyl, and propyl. In some aspect, the compound of the present application having the structure of formula (1), wherein each $R^2$ is independently selected from methyl, ethyl, and propyl. In certain aspect, the compound of the present application having the structure of formula (I), wherein $R^3$ is hydrogen, methyl, ethyl, propyl, butyl, cyclopropyl, or cyclobutyl. In other aspect, the compound of the present application having the structure of formula (I), wherein $R^5$ is hydrogen, methyl, ethyl, or propyl. In some other aspect, the compound of the present application having the structure of formula (1), wherein $R^5$ and $R^3$ together with the atoms to which they are attached optionally form pyrrolidinyl. In further aspect, the compound of the present application having the structure of formula (1), wherein $R^4$ is a monocyclic heteroaryl having at least two nitrogen atoms, wherein $R^4$ is substituted with two or three members independently selected from bromo, chloro, fluoro, cyano, methyl, ethyl, propyl, and —$NH_2$. In some further aspect, the compound of the present application having the structure of formula (I), wherein $R^4$ is pyrimidinyl substituted with two or three members selected from the group consisting of bromo, chloro, fluoro, cyano, methyl, ethyl, propyl, and —$NH_2$.

In certain embodiments, the PI3K inhibitors are the compounds selected from Table 1, a pharmaceutically acceptable salt, isomer, or a mixture thereof. In additional embodiments, the compound is an (S)-enantiomer. In other embodiments, the compound is an (R)-enantiomer. In other additional embodiments, the compound is an atropisomer.

The application also provides a pharmaceutical composition that comprises a compound of formula (I), a pharmaceutically acceptable salt, isomer, or a mixture thereof, together with at least one pharmaceutically acceptable vehicle. Examples of a pharmaceutically acceptable vehicle may be selected from carriers, adjuvants, and excipients.

Further provided herein is a method of treating a disease, disorder, or condition in a human in need thereof by administering to the human a therapeutically effective amount of a compound of formula (I) or a pharmaceutically acceptable salt, isomer, or a mixture thereof. Further provided is a compound of formula (I) for use in a method of treating a disease, disorder or condition that is mediated by PI3K isoforms. The application also provides the use of a compound of formula (L) in the manufacture of a medicament for the treatment of a disease, disorder or condition that is mediated by PI3K isoforms. In certain embodiments, the disease, disorder, or condition is associated or mediated by PI3K. In some embodiments, the disease, disorder, or condition is an inflammatory disorder. In other embodiments, the disease, disorder, or condition is a cancer.

Also provided herein is a method of inhibiting the activity of a phosphatidylinositol 3-kinase polypeptide by contacting the polypeptide with a compound of formula (1) or a pharmaceutically acceptable salt, isomer, or a mixture thereof.

Further provided is a method of inhibiting excessive or destructive immune reactions, comprising administering an effective amount of a compound of formula (I) or a pharmaceutically acceptable salt, isomer, or a mixture thereof.

Also provided is a method of inhibiting growth or proliferation of cancer cells comprising contacting the cancer cells with an effective amount of a compound of formula (1) or a pharmaceutically acceptable salt, isomer, or a mixture thereof Also provided is a kit that includes a compound of formula (I) or a pharmaceutically acceptable salt, isomer, or a mixture thereof. The kit may further comprise a label and/or instructions for use of the compound in treating a disease, disorder, or condition in a human in need thereof. In some embodiments, the disease, disorder, or condition may be associated or mediated by PI3K activity.

Also provided are articles of manufacture that include a compound of formula (I) or a pharmaceutically acceptable salt, isomer, or a mixture thereof, and a container. In one embodiment, the container may be a vial, jar, ampoule, preloaded syringe, or an intravenous bag.

DETAILED DESCRIPTION

The following description sets forth exemplary methods, parameters and the like. Such description is not intended as a limitation on the scope of the present application but is instead provided as exemplary embodiments.

As used herein, the following words, phrases and symbols are generally intended to have the meanings as set forth below, except to the extent that the context in which they are used indicates otherwise.

A dash ("-") that is not between two letters or symbols is used to indicate a point of attachment for a substituent. For example, —$CONH_2$ is attached through the carbon atom. A dash at the front or end of a chemical group is a matter of convenience; chemical groups may be depicted with or without one or more dashes without losing their ordinary meaning. A wavy line drawn through a line in a structure indicates a point of attachment of a group. Unless chemically or structurally required, no directionality is indicated or implied by the order in which a chemical group is written or named.

The prefix "$C_{u-v}$" indicates that the following group has from u to v carbon atoms. For example, "$C_{1-6}$ alkyl" indicates that the alkyl group has from 1 to 6 carbon atoms.

Reference to "about" a value or parameter herein includes (and describes) embodiments that are directed to that value or parameter per se. In certain embodiments, the term "about" includes the indicated amount±10%. In other embodiments, the term "about" includes the indicated amount±5%. In certain other embodiments, the term "about" includes the indicated amount±1%. Also, to the term "about X" includes description of "X". Also, the singular forms "a" and "the" include plural references unless the context clearly dictates otherwise. Thus, e.g., reference to "the compound" includes a plurality of such compounds and reference to "the assay" includes reference to one or more assays and equivalents thereof known to those skilled in the art.

"Alkyl" refers to an unbranched or branched saturated hydrocarbon chain. As used herein, alkyl has 1 to 20 carbon atoms (i.e., $C_{1-20}$ alkyl), 1 to 8 carbon atoms (i.e., $C_{1-8}$ alkyl), 1 to 6 carbon atoms (i.e., $C_{1-6}$ alkyl), or 1 to 4 carbon atoms (i.e., $C_{1-4}$ alkyl). Examples of alkyl groups include methyl, ethyl, propyl, isopropyl, n-butyl, sec-butyl, iso-butyl, tert-butyl, pentyl, 2-pentyl, isopentyl, neopentyl, hexyl, 2-hexyl, 3-hexyl, and 3-methylpentyl. When an alkyl residue having a specific number of carbons is named, all geometric isomers having that number of carbons may be encompassed; thus, for example, "butyl" includes n-butyl, sec-butyl, isobutyl and t-butyl; "propyl" includes n-propyl and isopropyl.

"Alkenyl" refers to an aliphatic group containing at least one carbon-carbon double bond and having from 2 to 20 carbon atoms (i.e., $C_{2-20}$ alkenyl), 2 to 8 carbon atoms (i.e., $C_{2-8}$ alkenyl), 2 to 6 carbon atoms (i.e., $C_{2-6}$ alkenyl), or 2 to 4 carbon atoms (i.e., $C_{2-4}$ alkenyl). Examples of alkenyl groups include ethenyl, propenyl, butadienyl (including 1,2-butadienyl and 1,3-butadienyl).

"Alkynyl" refers to an aliphatic group containing at least one carbon-carbon triple bond and having from 2 to 20 carbon atoms (i.e., $C_{2-20}$ alkynyl), 2 to 8 carbon atoms (i.e., $C_{2-8}$ alkynyl), 2 to 6 carbon atoms (i.e., $C_{2-6}$ alkynyl), or 2 to 4 carbon atoms (i.e., $C_{2-4}$ alkynyl). The term "alkynyl" also includes those groups having one triple bond and one double bond.

"Alkoxy" refers to the group "alkyl-O-". Examples of alkoxy groups include methoxy, ethoxy, n-propoxy, iso-propoxy, n-butoxy, tert-butoxy, sec-butoxy, n-pentoxy, n-hexoxy, and 1,2-dimethylbutoxy.

"Acyl" refers to a group —C(=O)R, wherein R is hydrogen, alkyl, cycloalkyl, heterocycloalkyl, aryl, heteroalkyl, or heteroaryl; each of which may be optionally substituted, as defined herein. Examples of acyl include formyl, acetyl, cylcohexylcarbonyl, cyclohexylmethyl-carbonyl, and benzoyl.

"Amido" refers to both a "C-amido" group which refers to the group —C(=))$NR^yR^z$ and an "N-amido" group which refers to the group —$NR^yC$(=O)$R^z$, wherein $R^y$ and $R^z$ are independently selected from the group consisting of hydrogen, alkyl, aryl, haloalkyl, or heteroaryl; each of which may be optionally substituted.

"Amino" refers to the group —$NR^yR^z$ wherein $R^y$ and $R^z$ are independently selected from the group consisting of hydrogen, alkyl, haloalkyl, aryl, or heteroaryl; each of which may be optionally substituted.

"Aryl" refers to an aromatic carbocyclic group having a single ring (e.g. monocyclic) or multiple rings (e.g. bicyclic or tricyclic) including fused systems. As used herein, aryl has 6 to 20 ring carbon atoms (i.e., $C_{6-20}$ aryl), 6 to 12 carbon ring atoms (i.e., $C_{6-12}$ aryl), or 6 to 10 carbon ring atoms (i.e., $C_{6-10}$ aryl). Examples of aryl groups include phenyl, naphthyl, fluorenyl, and anthryl. Aryl, however, does not encompass or overlap in any way with heteroaryl defined below. If one or more aryl groups are fused with a heteroaryl ring, the resulting ring system is heteroaryl.

"Cyano" or "carbonitrile" refers to the group —CN.

"Cycloalkyl" refers to a saturated or partially saturated cyclic alkyl group having a single ring or multiple rings including fused, bridged, and spiro ring systems. The term "cycloalkyl" includes cycloalkenyl groups (i.e. the cyclic group having at least one alkenyl). As used herein, cycloalkyl has from 3 to 20 ring carbon atoms (i.e., $C_{3-20}$ cycloalkyl), 3 to 12 ring carbon atoms (i.e., $C_{3-12}$ cycloalkyl), 3 to 10 ring carbon atoms (i.e., $C_{3-10}$ cycloalkyl), 3 to 8 ring carbon atoms (i.e., $C_{3-8}$ cycloalkyl), or 3 to 6 ring carbon atoms (i.e., $C_{3-6}$ cycloalkyl). Examples of cycloalkyl groups include cyclopropyl, cyclobutyl, cyclopentyl, and cyclohexyl.

"Halogen" or "halo" includes fluoro, chloro, bromo, and iodo. "Haloalkyl" refers to an unbranched or branched alkyl group as defined above, wherein one or more hydrogen atoms are replaced by a halogen. For example, where a residue is substituted with more than one halogen, it may be referred to by using a prefix corresponding to the number of halogen moieties attached. Dihaloalkyl and trihaloalkyl refer to alkyl substituted with two ("di") or three ("tri") halo groups, which may be, but are not necessarily, the same halogen. Examples of haloalkyl include difluoromethyl (—$CHF_2$) and trifluoromethyl (—$CF_3$).

"Heteroalkyl" refers to an alkyl group in which one or more of the carbon atoms (and any associated hydrogen atoms) are each independently replaced with the same or different heteroatomic group. By way of example, 1, 2 or 3 carbon atoms may be independently replaced with the same or different heteroatomic group. Heteroatomic groups include, but are not limited to, —NR—, —O—, —S—, —S(O)—, —$S(O)_2$—, and the like, where R is H, alkyl, aryl, cycloalkyl, heteroalkyl, heteroaryl or heterocycloalkyl, each of which may be optionally substituted. Examples of heteroalkyl groups include —$OCH_3$, —$CH_2OCH_3$, —$SCH_3$, —$CH_2SCH_3$, —$NRCH_3$, and —$CH_2NRCH_3$, where R is hydrogen, alkyl, aryl, arylalkyl, heteroalkyl, or heteroaryl, each of which may be optionally substituted. As used herein, heteroalkyl include 1 to 10 carbon atoms, 1 to 8 carbon atoms, or 1 to 4 carbon atoms; and 1 to 3 heteroatoms, 1 to 2 heteroatoms, or 1 heteroatom.

"Heteroaryl" refers to an aromatic group having a single ring, multiple rings, or multiple fused rings, with one or more ring heteroatoms independently selected from nitrogen, oxygen, and sulfur. As used herein, heteroaryl include 1 to 20 ring carbon atoms (i.e., $C_{1-20}$ heteroaryl), 3 to 12 ring carbon atoms (i.e., $C_{3-12}$ heteroaryl), or 3 to 8 carbon ring atoms (i.e., $C_3$, heteroaryl); and 1 to 5 heteroatoms, 1 to 4 heteroatoms, 1 to 3 ring heteroatoms, 1 to 2 ring heteroatoms, or 1 ring heteroatom independently selected from nitrogen, oxygen, and sulfur. Examples of heteroaryl groups include pyrimidinyl, purinyl, pyridyl, pyridazinyl, benzothiazolyl, and pyrazolyl. Heteroaryl does not encompass or overlap with aryl as defined above.

"Heterocycloalkyl" refers to a saturated or unsaturated cyclic alkyl group, with one or more ring heteroatoms independently selected from nitrogen, oxygen and sulfur. The term "heterocycloalkyl" includes heterocycloalkenyl groups (i.e. the heterocycloalkyl group having at least one alkenyl). A heterocycloalkyl may be a single ring or multiple rings wherein the multiple rings may be fused, bridged, or spiro. As used herein, heterocycloalkyl has 2 to 20 ring carbon atoms (i.e., $C_{2-20}$ heterocycloalkyl), 2 to 12 ring carbon atoms (i.e., $C_{2-12}$ heterocycloalkyl), 2 to 10 ring carbon atoms (i.e., $C_{2-10}$ heterocycloalkyl), 2 to 8 ring carbon atoms (i.e., $C_{2-20}$ heterocycloalkyl), 3 to 12 ring carbon atoms (i.e., $C_{3-12}$ heterocycloalkyl), 3 to 8 ring carbon atoms (i.e., $C_{3-8}$ heterocycloalkyl), or 3 to 6 ring carbon atoms (i.e., $C_{3-6}$ heterocycloalkyl); having 1 to 5 ring heteroatoms, 1 to 4 ring heteroatoms, 1 to 3 ring heteroatoms, 1 to 2 ring heteroatoms, or 1 ring heteroatom independently selected from nitrogen, sulfur or oxygen. Examples of heterocycloalkyl groups include pyrrolidinyl, piperidinyl, piperazinyl, oxetanyl, dioxolanyl, azetidinyl, and morpholinyl.

"Hydroxy" or "hydroxyl" refers to the group —OH.

"Oxo" refers to the group (=O) or (O).

"Sulfonyl" refers to the group —$S(O)_2R$, where R is alkyl, haloalkyl, cycloalkyl, heterocycloalkyl, heteroaryl, or aryl. Examples of sulfonyl are methylsulfonyl, ethylsulfonyl, phenylsulfonyl, and toluenesulfonyl.

Certain commonly used alternative chemical names may be used. For example, a divalent group such as a divalent "alkyl" group, a divalent "aryl" group, etc., may also be referred to as an "alkylene" group or an "alkylenyl" group, an "arylene" group or an "arylenyl" group, respectively. Also, unless indicated explicitly otherwise, where combinations of groups are referred to herein as one moiety, e.g.

arylalkyl, the last mentioned group contains the atom by which the moiety is attached to the rest of the molecule.

The terms "optional" or "optionally" means that the subsequently described event or circumstance may or may not occur, and that the description includes instances where said event or circumstance occurs and instances in which it does not. Also, the term "optionally substituted" refers to any one or more hydrogen atoms on the designated atom or group may or may not be replaced by a moiety other than hydrogen.

The term "substituted" means that any one or more hydrogen atoms on the designated atom or group is replaced with one or more substituents other than hydrogen, provided that the designated atom's normal valence is not exceeded. The one or more substituents include, but are not limited to, alkyl, alkenyl, alkynyl, alkoxy, acyl, amino, amido, amidino, aryl, azido, carbamoyl, carboxyl, carboxyl ester, cyano, guanidino, halo, haloalkyl, heteroalkyl, heteroaryl, heterocycloalkyl, hydroxy, hydrazino, imino, oxo, nitro, alkylsulfinyl, sulfonic acid, alkylsulfonyl, thiocyanate, thiol, thione, or combinations thereof. By way of example, there may be one, two, three, four, five, or six substituents. Polymers or similar indefinite structures arrived at by defining substituents with further substituents appended ad infinitum (e.g., a substituted aryl having a substituted alkyl which is itself substituted with a substituted aryl group, which is further substituted by a substituted heteroalkyl group, etc.) are not intended for inclusion herein. Unless otherwise noted, the maximum number of serial substitutions in compounds described herein is three. For example, serial substitutions of substituted aryl groups with two other substituted aryl groups are limited to substituted aryl (substituted aryl) substituted aryl. Similarly, the above definitions are not intended to include impermissible substitution patterns (e.g., methyl substituted with 5 fluorines or heteroaryl groups having two adjacent oxygen ring atoms). Such impermissible substitution patterns are well known to the skilled artisan. When used to modify a chemical group, the term "substituted" may describe other chemical groups defined herein. For example, the term "substituted aryl" includes, but is not limited to, "alkylaryl." Unless specified otherwise, where a group is described as optionally substituted, any substituents of the group are themselves unsubstituted.

In some embodiments, the term "substituted alkyl" refers to an alkyl group having one or more substituents including hydroxyl, halo, alkoxy, cycloalkyl, heterocycloalkyl, aryl, and heteroaryl. In additional embodiments, "substituted cycloalkyl" refers to a cycloalkyl group having one or more substituents including alkyl, haloalkyl, heterocycloalkyl, aryl, heteroaryl, alkoxy, halo, hydroxyl; "substituted aryl" refers to an aryl group having one or more substituents including halo, alkyl, haloalkyl, heterocycloalkyl, heteroaryl, alkoxy, and cyano, and "substituted sulfonyl" refers to a group —S(O)$_2$R, in which R is substituted with one or more substituents of alkyl, cycloalkyl, heterocycloalkyl, aryl, or heteroaryl. In other embodiments, the one or more substituents may be further substituted with halo, alkyl, haloalkyl, alkoxy, cycloalkyl, heterocycloalkyl, aryl, or heteroaryl, each of which is substituted. In additional embodiments, the substituents may be further substituted with halo, alkyl, haloalkyl, alkoxy, cycloalkyl, heterocycloalkyl, aryl, or heteroaryl, each of which is unsubstituted.

PI3K Inhibitor Compounds

The present application provides the compounds that function as inhibitors of PI3K isoforms. In one aspect, the PI3K inhibitors are the compounds having the structure of formula (J):

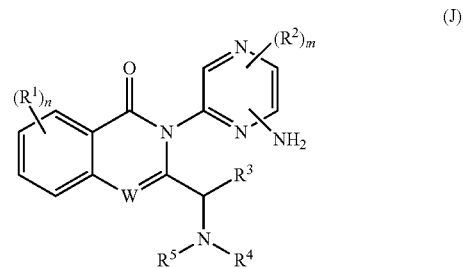

wherein:
n is 0, 1, 2, 3, or 4;
m is 0, 1, or 2;
W is CH or N;
each $R^1$ is independently selected from halo, cyano, optionally substituted alkyl, optionally substituted haloalkyl, optionally substituted alkoxy, optionally substituted sulfonyl, optionally substituted aryl, optionally substituted heteroaryl, optionally substituted cycloalkyl, optionally substituted heterocycloalkyl;
each $R^2$ is independently selected from halo, optionally substituted alkyl, optionally substituted haloalkyl;
$R^3$ is hydrogen, optionally substituted alkyl, optionally substituted haloalkyl, optionally substituted cycloalkyl, or optionally substituted aryl;
$R^4$ is heteroaryl optionally substituted with one, two, or three members independently selected from halo, cyano, optionally substituted haloalkyl, optionally substituted alkyl, and —NH$_2$; and
$R^5$ is hydrogen or optionally substituted alkyl, wherein $R^5$ and $R^3$ together with the atoms to which they are attached optionally form a heterocyclic ring;
or a pharmaceutically acceptable salt, isomer, or a mixture thereof.

The application also provides the compounds having the structure of formula (I) that function as inhibitors of PI3K isoforms. In one embodiment, the PI3K inhibitors are the compounds of the formula (I) having the structure of

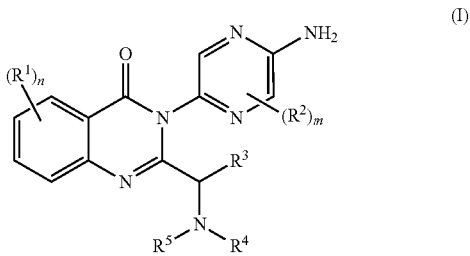

wherein:
n is 1, 2, or 3;
m is 0 or 1;
each $R^1$ is independently selected from halo, cyano, optionally substituted $C_{1-6}$ alkyl, optionally substituted $C_{1-6}$ haloalkyl, optionally substituted $C_{1-6}$ alkoxy, optionally substituted sulfonyl, optionally substituted $C_{3-8}$ aryl, optionally substituted $C_{3-8}$ heteroaryl, optionally substituted $C_{3-8}$ cycloalkyl, and optionally substituted $C_{3-8}$ heterocycloalkyl;

each $R^2$ is independently selected from halo and optionally substituted $C_{1-6}$ alkyl;

$R^3$ is hydrogen, optionally substituted $C_{1-6}$ alkyl, optionally substituted $C_{6-10}$ aryl, or optionally substituted $C_{3-8}$ cycloalkyl:

$R^4$ is a six- to twelve-membered heteroaryl having at least one aromatic group and at least two heteroatoms, wherein the heteroatoms are selected from N, O, or S, wherein the heteroaryl is optionally substituted with one, two, or three members independently selected from halo, cyano, optionally substituted haloalkyl, optionally substituted $C_{1-6}$ alkyl, and —$NH_2$; and $R^5$ is hydrogen or optionally substituted $C_{1-6}$ alkyl, wherein $R^5$ and $R^3$ together with the atoms to which they are attached optionally form a four- or eight-membered heterocyclic ring;

or a pharmaceutically acceptable salt, isomer, or a mixture thereof.

In some embodiment, the compounds have the structure of formula (I) wherein n is 1 or 2;

m is 0 or 1;

each $R^1$ is independently selected from halo, $C_{1-6}$ alkyl, and $C_{1-6}$ haloalkyl;

each $R^2$ is $C_{1-6}$ alkyl;

$R^3$ is hydrogen, $C_{1-6}$ alkyl, or $C_{3-8}$ cycloalkyl;

$R^4$ is a six- to twelve-membered heteroaryl having at least one aromatic ring and at least two nitrogen atoms, wherein the heteroaryl is optionally substituted with one, two, or three members independently selected from halo, cyano, —$NH_2$, $C_{1-6}$ haloalkyl, and $C_{1-6}$ alkyl; and $R^5$ is hydrogen, methyl, ethyl, or propyl, or $R^5$ and $R^3$ together with the atoms to which they are attached optionally form a five-membered heterocyclic ring;

or a pharmaceutically acceptable salt, isomer, or a mixture thereof

In some embodiment, the compound having the structure of the formula (I) wherein:

n is 1 or 2;

m is 0 or 1;

each $R^1$ is independently selected from chloro, bromo, fluoro, methyl, ethyl, and propyl;

each $R^2$ is independently selected from methyl, ethyl, and propyl;

$R^3$ is hydrogen, methyl, ethyl, propyl, butyl, cyclopropyl, or cyclobutyl;

$R^4$ is a six- to twelve-membered monocyclic heteroaryl having at least one aromatic ring and at least two nitrogen atoms, wherein the monocyclic heteroaryl is substituted with two or three members independently selected from bromo, chloro, fluoro, cyano, methyl, ethyl, propyl, and —$NH_2$; and $R^5$ is hydrogen; or a pharmaceutically acceptable salt, isomer, or a mixture thereof.

In some embodiment, the compound having the structure of the formula (I) wherein:

n is 1 or 2;

m is 0;

each $R^1$ is independently selected from chloro, bromo, fluoro, methyl, ethyl, and propyl;

$R^3$ is hydrogen, methyl, ethyl, propyl, butyl, cyclopropyl, or cyclobutyl;

$R^4$ is a six- to twelve-membered bicyclic heteroaryl having at least one aromatic ring, at least two nitrogen atoms, and at least one heteroatoms selected from N, O, and S, wherein the bicyclic heteroaryl is optionally substituted with one or two members independently selected from bromo, chloro, fluoro, cyano, methyl, ethyl, propyl, and —$NH_2$; and $R^5$ is hydrogen;

or a pharmaceutically acceptable salt, isomer, or a mixture thereof.

In some embodiment, the compound having the structure of the formula (I) wherein:

n is 1 or 2;

m is 0:

each $R^1$ is independently selected from chloro, bromo, fluoro, methyl, ethyl, and propyl;

$R^4$ is pyrimidinyl substituted with two or three members independently selected from bromo, chloro, fluoro, cyano, methyl, ethyl, propyl, and —$NH_2$; and $R^5$ is hydrogen;

or a pharmaceutically acceptable salt, isomer, or a mixture thereof.

In some additional embodiment, the compounds have the structure of the formula (I) wherein:

n is 1 or 2;

m is 0 or 1;

each $R^1$ is independently selected from chloro, bromo, fluoro, methyl, ethyl, and propyl;

each $R^2$ is independently selected from methyl, ethyl, and propyl;

$R^3$ is hydrogen, methyl, ethyl, propyl, butyl, cyclopropyl, or cyclobutyl;

$R^4$ is a six- to twelve-membered monocyclic heteroaryl having at least one aromatic ring and at least two nitrogen atoms, wherein the monocyclic heteroaryl is substituted with two or three members independently selected from bromo, chloro, fluoro, cyano, methyl, ethyl, propyl, fluoromethyl, difluoromethyl, trifluoromethyl, fluoroethyl, difluoroethyl, trifluoroethyl, fluoropropyl, difluoropropyl, trifluoropropyl, and —$NH_2$; and $R^5$ is hydrogen;

or a pharmaceutically acceptable salt, isomer, or a mixture thereof.

In some embodiment, the compounds have the structure of the formula (I) wherein:

n is 1 or 2;

m is 0;

each $R^1$ is independently selected from chloro, bromo, fluoro, methyl, ethyl, and propyl;

$R^3$ is hydrogen, methyl, ethyl, propyl, butyl, cyclopropyl, or cyclobutyl;

$R^4$ is a six- to twelve-membered bicyclic heteroaryl having at least one aromatic ring, at least two nitrogen atoms, and at least one heteroatoms selected from N, O, and S, wherein the bicyclic heteroaryl is optionally substituted with one or two members independently selected from bromo, chloro, fluoro, cyano, methyl, ethyl, propyl, fluoromethyl, difluoromethyl, trifluoromethyl, fluoroethyl, difluoroethyl, trifluoroethyl, fluoropropyl, difluoropropyl, trifluoropropyl, and —$NH_2$; and $R^5$ is hydrogen;

or a pharmaceutically acceptable salt, isomer, or a mixture thereof.

In some embodiment, the compounds have the structure of the formula (I) wherein:

n is 1 or 2;

m is 0;

each $R^1$ is independently selected from chloro, bromo, fluoro, methyl, ethyl, and propyl:

$R^4$ is pyrimidinyl substituted with two or three members independently selected from bromo, chloro, fluoro, cyano, methyl, ethyl, propyl, fluoromethyl, difluoromethyl, trifluoromethyl, fluoroethyl, difluoroethyl, trifluoroethyl, fluoropropyl, difluoropropyl, trifluoropropyl and —$NH_2$; and R⁵ is hydrogen;
or a pharmaceutically acceptable salt, isomer, or a mixture thereof.

In some embodiment, the compounds have the structure of the formula (I) wherein:
n is 1 or 2;
m is 0;
each R¹ is independently selected from chloro, bromo, fluoro, methyl, ethyl, and propyl;
R⁴ is pyrimidinyl substituted with two or three members, each of which is independently selected from fluoromethyl, difluoromethyl, trifluoromethyl, fluoroethyl, difluoroethyl, trifluoroethyl, fluoropropyl, difluoropropyl, trifluoropropyl and —NH₂; and
R⁵ is hydrogen;
or a pharmaceutically acceptable salt, isomer, or a mixture thereof.

Also, the compounds of formulae (J) or (I) may have the structure of formula (Ia):

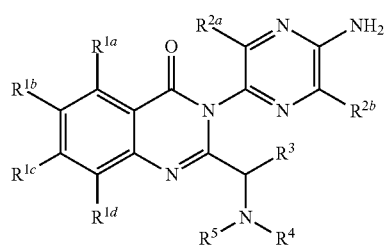

(Ia)

wherein
each R¹ᵃ, R¹ᵇ, R¹ᶜ, and R¹ᵈ is independently selected from hydrogen, fluoro, chloro, bromo, and iodo;
each R²ᵃ and R²ᵇ is independently selected from hydrogen, methyl, ethyl, and propyl; and
R⁴ is selected from

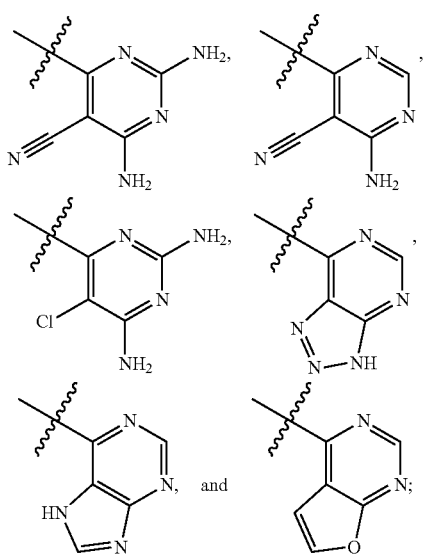

or a pharmaceutically acceptable salt, isomer, or a mixture thereof, wherein R⁴ is optionally substituted with one, two, or three members independently selected from chloro, fluoro, bromo, iodo, methyl, ethyl, propyl, cyano, and —NH₂; and R³ and R⁵ are described herein;
or a pharmaceutically acceptable salt, isomer, or a mixture thereof.

In certain embodiment, the compounds have the structure of formula (Ia), wherein
each R¹ᵃ, R¹ᵇ, R¹ᶜ, and R¹ᵈ is independently selected from hydrogen, fluoro, chloro, bromo, and iodo;
each R²ᵃ and R²ᵇ is independently selected from hydrogen, methyl, ethyl, and propyl; and
R³ is selected from hydrogen, methyl, ethyl, propyl, butyl, cyclopropyl, and cyclobutyl:
R⁴ is selected from

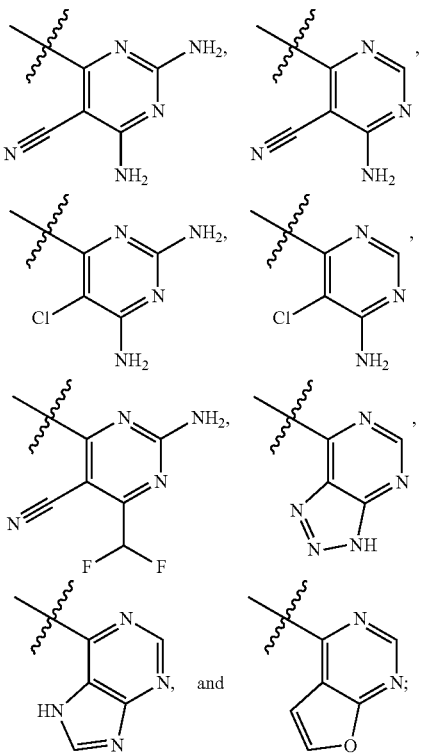

and
R⁵ is hydrogen;
or a pharmaceutically acceptable salt, isomer, or a mixture thereof.

In certain embodiment, the compounds have the structure of formula (Ia), wherein
each R¹ᵃ, R¹ᵇ, R¹ᶜ, and R¹ᵈ is independently selected from hydrogen, fluoro, chloro, bromo, and iodo;
each R²ᵃ and R²ᵇ is independently selected from hydrogen, methyl, ethyl, and propyl;
R³ is selected from hydrogen, methyl, ethyl, propyl, butyl, cyclopropyl, and cyclobutyl;
R⁴ is selected from

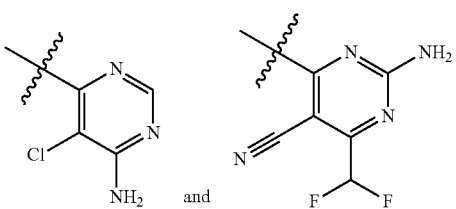 [SMILES: *c1ncnc(N)c1Cl ; *c1nc(N)nc(C(F)F)c1C#N]

and

R$^5$ is hydrogen;

or a pharmaceutically acceptable salt, isomer, or a mixture thereof.

The compounds of the formulae (J) or (I) may also have the structure of formula (Ib):

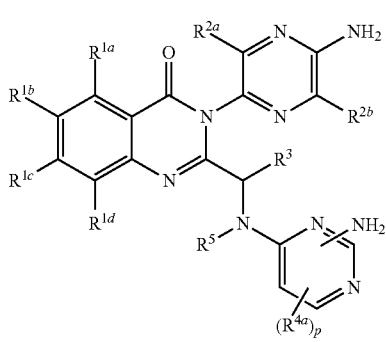

wherein

R$^{1a}$, R$^{1b}$, R$^{1c}$, R$^{1d}$, R$^{2a}$, R$^{2b}$, R$^3$ and R$^5$ are defined herein;

p is 0, 1, or 2; and

R$^{4a}$ is independently selected from halo, cyano, —NH$_2$, and C$_{1-6}$ alkyl;

or a pharmaceutically acceptable salt, isomer, or a mixture thereof.

In certain embodiment, the compounds have the structure of the formula (Ib), wherein R$^{1a}$, R$^{1b}$, R$^{1c}$, R$^{1d}$, R$^{2a}$, R$^{2b}$, R$^3$ and R$^5$ are defined herein;

p is 0, 1, or 2; and each R$^{4a}$ is independently selected from halo, cyano, —NH$_2$, C$_{1-6}$ haloalkyl, and C$_{1-6}$ alkyl;

or a pharmaceutically acceptable salt, isomer, or a mixture thereof.

In certain embodiment, the compounds have the structure of the formula (Ib), wherein each R$^{1a}$, R$^{1b}$, R$^{1c}$, R$^{1d}$ is independently selected from hydrogen, fluoro, chloro, bromo, and iodo;

each R$^{2a}$ and R$^{2b}$ is independently selected from hydrogen, methyl, ethyl, and propyl; and R$^3$ is selected from hydrogen, methyl, ethyl, propyl, butyl, cyclopropyl, and cyclobutyl;

p is 1 or 2; and each R$^{4a}$ is independently selected from bromo, chloro, fluoro, cyano, methyl, ethyl, propyl, fluoromethyl, difluoromethyl, trifluoromethyl, fluoroethyl, difluoroethyl, trifluoroethyl, fluoropropyl, difluoropropyl, trifluoropropyl, and —NH$_2$;

or a pharmaceutically acceptable salt, isomer, or a mixture thereof.

In certain embodiment, the compounds have the structure of the formula (Ib), wherein each R$^{1a}$, R$^{1b}$, R$^{1c}$, R$^{1d}$ is independently selected from hydrogen, fluoro, chloro, bromo, and iodo;

each R$^{2a}$ and R$^{2b}$ is independently selected from hydrogen, methyl, ethyl, and propyl; and R$^3$ is selected from hydrogen, methyl, ethyl, propyl, butyl, cyclopropyl, and cyclobutyl;

p is 1 or 2; and each R$^{4a}$ is independently selected from fluoromethyl, difluoromethyl, trifluoromethyl, fluoroethyl, difluoroethyl, trifluoroethyl, fluoropropyl, difluoropropyl, trifluoropropyl, and —NH$_2$;

or a pharmaceutically acceptable salt, isomer, or a mixture thereof

In one embodiment, n is 0. In some embodiments, n is 1, 2, 3, or 4. In some embodiments, n is 1, 2, or 3. In other embodiments, n is 1 or 2. In certain embodiments, n is 1 and R$^1$ moiety may be located on any position of the phenyl of the quinazolinone ring. In another embodiment, n is 2. Both R$^1$ substituents or moieties may be the same or different. Two R$^1$ moieties may be located on any two positions of the phenyl of the quinazolinone ring. By way of example, the first R$^1$ may be ortho, meta, or para to the second R$^1$. In yet another embodiment, n is 3. All R$^1$ substituents or moieties may be the same or different, or two R$^1$ may be the same and different from the third R$^1$. Three R$^1$ moieties may be located on any three positions of the phenyl of the quinazolinone ring. For example, the first R$^1$ may be ortho to the second R$^1$, and the first R$^1$ may be para to the third R$^1$. In yet another embodiment, n is 4. All R$^1$ substituents may be the same or different, three R$^1$ may be the same and different from the fourth R$^1$, two R$^1$ may be the same and different from the third and the fourth R$^1$.

In some other embodiments, each R$^1$ is independently halo, cyano, optionally substituted C$_{1-6}$ alkyl, optionally substituted C$_{1-6}$ haloalkyl, optionally substituted C$_{1-6}$ alkoxy, hydroxy, optionally substituted C$_{3-6}$ cycloalkyl, optionally substituted C$_{3-6}$ heterocycloalkyl, optionally substituted C$_{6-10}$ aryl, optionally substituted C$_{4-8}$ heteroaryl, or optionally substituted C$_{1-6}$ alkylsulfonyl. In certain embodiments, each R$^1$ is independently halo, cyano, optionally substituted C$_{1-4}$ alkyl, optionally substituted C$_{1-4}$haloalkyl, optionally substituted C$_{1-4}$ alkoxy, optionally substituted C$_{3-6}$ cycloalkyl, or optionally substituted C$_{1-4}$ alkylsulfonyl. In other embodiments, each R$^1$ is independently halo, cyano, C$_{1-4}$ haloalkyl, C$_{1-4}$ alkyl, or C$_{1-4}$ alkylsulfonyl. In certain embodiments, each R$^1$ is independently selected from fluoro, chloro, iodo, bromo, cyano, methyl, ethyl, propyl, butyl, fluoromethyl, fluoroethyl, difluoromethyl, difluoroethyl, trifluoromethyl, trifluoroethyl, methylsulfonyl, ethylsulfonyl, or propylsulfonyl. In some embodiments, each R$^1$ is independently fluoro, chloro, iodo, cyano, methyl, ethyl, difluoromethyl (—CHF$_2$), trifluoromethyl (—CF$_3$), methoxy, methylsulfonyl (—SO$_2$CH$_3$), cyclopropylmethyl, or cyclopropyl. In one embodiment, each R$^1$ is independently fluoro, chloro, cyano, methylsulfonyl, methyl, or trifluoromethyl.

In certain embodiments, m is 0. In some embodiments, m is 0, 1, or 2. In some other embodiments, m is 1 or 2. When m is 1, R$^2$ substituent or moiety may be located on any position of the pyrazine ring. When m is 2, both R$^2$ substituents may be the same or different.

In certain embodiments, each R$^2$ is independently halo, cyano, optionally substituted C$_{1-6}$ alkyl, and optionally substituted C$_{1-6}$ haloalkyl. In some embodiments, each R$^2$ is independently halo, cyano, C$_{1-4}$ alkyl, and C$_{1-4}$ haloalkyl. In some other embodiments, each R$^2$ is independently fluoro, chloro, iodo, methoxy, ethoxy, propoxy, butoxy, pentoxy, hexoxy, fluoromethyl (e.g. —CH$_2$F), difluoromethyl (e.g. —CHF$_2$), trifluoromethyl (e.g. —CF$_3$), fluoroethyl, difluoroethyl, trifluoroethyl, methyl, ethyl, propyl, or butyl. In one embodiment, each R$^2$ is independently fluoro, chloro, methyl, —CHF$_2$, or —CF$_3$.

In certain embodiment, R$^3$ is hydrogen, optionally substituted C$_{1-6}$ alkyl, optionally substituted C$_{3-8}$ cycloalkyl, or optionally substituted C$_{6-10}$ aryl. In one embodiment, R$^3$ is hydrogen, C$_{1-4}$ alkyl, C$_{3-6}$ cycloalkyl, or C$_{6-10}$ aryl, wherein C$_{1-4}$ alkyl is optionally substituted with C$_{1-4}$ alkoxy, C$_{6-10}$ aryl, or C$_{3-6}$ cycloalkyl, wherein C$_{1-4}$ alkoxy is optionally substituted with $C_{6-10}$ aryl. In additional embodiments, $R^3$ is $C_{1-4}$ alkyl, $C_{3-6}$ cycloalkyl, or $C_{6-10}$ aryl, wherein $C_{1-4}$ alkyl is optionally substituted with $C_{1-4}$ alkoxy, $C_{6-10}$ aryl, or $C_{3-6}$ cycloalkyl, wherein $C_{1-4}$ alkoxy is optionally substituted with phenyl, cyclopropyl, or cyclobutyl. In some embodiments, $R^3$ is hydrogen, methyl, ethyl, propyl, butyl, methoxy, ethoxy, cyclopropylmethyl, cyclopropylbutyl, cyclobutylmethyl, cyclopropylethyl, phenyl, cyclopropyl, cyclobutyl, cyclopentyl, or cyclohexyl, wherein methoxy and ethoxy is substituted with phenyl, cyclopropyl or cyclobutyl. In other embodiments. $R^3$ is methyl, ethyl, cyclopropylmethyl, or cyclopropyl.

In additional embodiments, $R^5$ is hydrogen or optionally substituted $C_{1-6}$ alkyl. In some embodiments, $R^5$ is hydrogen or $C_{1-4}$ alkyl. In certain embodiments, $R^5$ is hydrogen, methyl, ethyl, propyl or butyl. In certain other embodiments, $R^5$ is hydrogen.

In further embodiments, $R^3$ and $R^5$ with the atoms to which they are attached (e.g. carbon and nitrogen, respectively) optionally form a heterocyclic ring which is optionally substituted with halo. In other embodiments, the $R^3$-$R^5$ heterocyclic ring is a four- to seven-membered ring. In some other embodiments, the $R^3$-$R^5$ heterocyclic ring is a four- to seven-membered ring optionally substituted with fluoro, chloro, bromo, or iodo. In certain other embodiments, the $R^3$-$R^5$ heterocyclic ring is azepanyl, azetidinyl, piperidinyl, and pyrrolidinyl. In some other embodiments, the $R^3$-$R^5$ heterocyclic ring is pyrrolidinyl. In one other embodiment, the $R^3$-$R^5$ heterocyclic ring is a five-membered heterocycloalkyl substituted with halo. In other additional embodiments, the $R^3$-$R^5$ heterocyclic ring is pyrrolidinyl substituted with fluoro, chloro, bromo, or iodo.

In certain embodiments, $R^3$ is hydrogen, optionally substituted $C_{1-6}$ alkyl, optionally substituted $C_{3-8}$ cycloalkyl, or optionally substituted $C_{6-10}$ aryl. In one embodiment, $R^3$ is hydrogen, $C_{3-6}$ cycloalkyl, $C_{6-10}$ aryl, or $C_{1-4}$ alkyl which is optionally substituted with hydroxyl, $C_{6-10}$ aryl$C_{1-4}$ alkoxy, or $C_{3-6}$ cycloalkyl. In some embodiments, $R^3$ is hydrogen, methyl, ethyl, propyl, butyl, cyclopropylmethyl, cyclopropylethyl, cyclobutylmethyl, cyclobutylethyl, cyclopropyl, cyclobutyl, cyclopentyl, cyclohexyl, —CH$_2$OH, —C$_2$H$_4$OH, —C$_3$H$_6$OH, benzyloxymethyl (i.e.

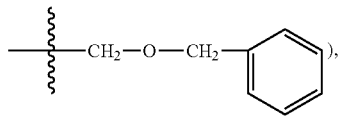

or phenyl (i.e

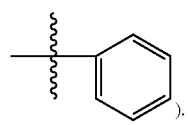 [SMILES: *c1ccccc1]

).

In further embodiments, $R^3$ and $R^5$ with the atoms to which they are attached (e.g. carbon and nitrogen, respectively) optionally form a heterocyclic ring. In other embodiments, the $R^3$-$R^5$ heterocyclic ring is a three- to eight-membered heterocycloalkyl (i.e. heterocycloalkyl having three to eight ring members and at least one ring member is a heteroatom). In other embodiments, the $R^3$-$R^5$ heterocyclic ring is a four- to seven-membered heterocycloalkyl (i.e. heterocycloalkyl having four to seven ring members and at least one ring member is a heteroatom). In one embodiment, the $R^3$-$R^5$ heterocyclic ring is a five-membered heterocycloalkyl. In certain other embodiments, the $R^3$-$R^5$ heterocyclic ring is $C_{3-8}$ heterocycloalkyl. In some other embodiments, the $R^3$-$R^5$ heterocyclic ring is pyrrolidinyl. In one other embodiment, the $R^3$-$R^5$ heterocyclic ring is a five-membered heterocycloalkyl substituted with one or two members of halo. In other additional embodiments, the $R^3$-$R^5$ heterocyclic ring is pyrrolidinyl substituted with one member of fluoro, chloro, bromo, or iodo.

In one embodiment. $R^4$ is heteroaryl having at least two nitrogen atoms and at least one aromatic ring, wherein $R^4$ heteroaryl is optionally substituted with one, two, or three members independently selected from halo, cyano, —NH$_2$, $C_{1-6}$ alkyl, and $C_{1-6}$ haloalkyl. In certain embodiments, $R^4$ heteroaryl is a six- to twelve-membered heteroaryl (i.e. heteroaryl having six to twelve ring members). In certain embodiments, $R^4$ heteroaryl is a six- to ten-membered heteroaryl (i.e. heteroaryl having six to ten ring members). $R^4$ heteroaryl may be a monocyclic or bicyclic heteroaryl. In some embodiments, $R^4$ heteroaryl is a monocyclic heteroaryl having at least two nitrogen atoms. In certain embodiments, $R^4$ hetroaryl is a bicyclic heteroaryl having at least one aromatic ring, at least two nitrogen atoms, and at least one additional heteroatom selected from N, O, or S. In certain other embodiments. $R^4$ heteroaryl is selected from purinyl, pyrimidinyl, thiazolopyrimidinyl, pyridopyrimidinyl, thienopyrimidinyl, pyrrolopyrimidinyl, furopyrimidinyl, or imidazotriazinyl.

In any of the foregoing formulae, $R^4$ is heteroaryl optionally substituted with one, two or three members independently selected from halo, cyano, —NH$_2$, $C_{1-6}$ alkyl, and $C_{1-6}$ haloalkyl, wherein the $R^4$ heteroaryl is selected from the group consisting of

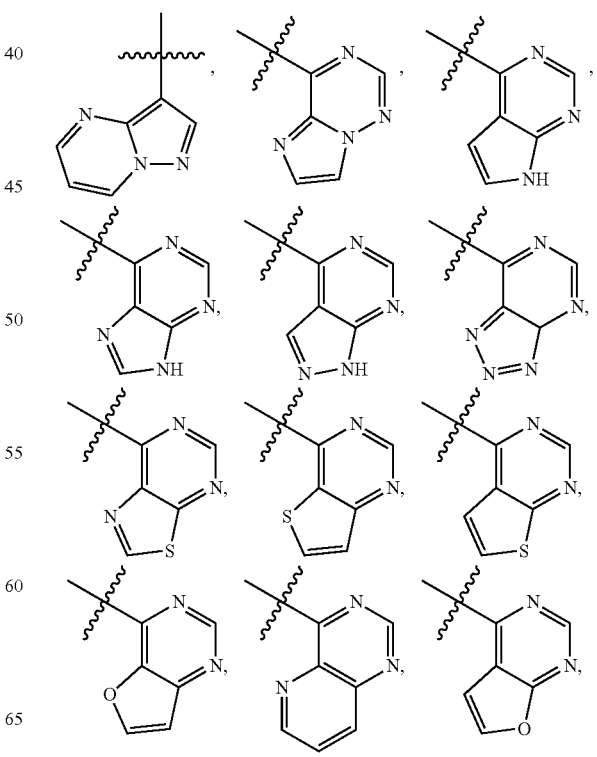

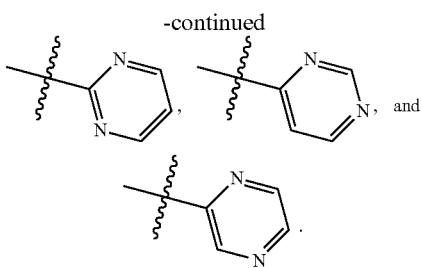

In certain other embodiments, $R^4$ is selected from purinyl, pyrimidinyl, thiazolopyrimidinyl, pyridopyrimidinyl, thienopyrimidinyl, pyrrolopyrimidinyl, furopyrimidinyl, and imidazotriazinyl, each of which is optionally substituted with one, two, or three members independently selected from chloro, fluoro, bromo, iodo, methyl, ethyl, propyl, cyano, and —$NH_2$. In other embodiments, $R^4$ is selected from purinyl, pyrimidinyl, thiazolopyrimidinyl, pyridopyrimidinyl, thienopyrimidinyl, pyrrolopyrimidinyl, furopyrimidinyl, and imidazotriazinyl, each of which is optionally substituted with one, two, or three members independently selected from chloro, fluoro, bromo, iodo, methyl, ethyl, propyl, cyano, fluoromethyl, difluormethyl, trifluoromethyl, fluoroethyl, difluoroethyl, trifluoroethyl, fluoropropyl, difluoropropyl, trifluoropropyl, and —$NH_2$. In certain other embodiments, $R^4$ is selected from thiazolopyrimidinyl, pyridopyrimidinyl, thienopyrimidinyl, pyrrolopyrimidinyl, furopyrimidinyl, and imidazotriazinyl, each of which is optionally substituted with two members independently selected from chloro, fluoro, bromo, iodo, methyl, ethyl, propyl, and —$NH_2$. In other embodiments, $R^4$ is selected from thiazolopyrimidinyl, pyridopyrimidinyl, thienopyrimidinyl, pyrrolopyrimidinyl, furopyrimidinyl, and imidazotriazinyl, each of which is optionally substituted with independently one member of chloro, fluoro, bromo, iodo, and —$NH_2$. In other embodiments, $R^4$ is selected from thiazolopyrimidinyl, pyridopyrimidinyl, thienopyrimidinyl, pyrrolopyrimidinyl, furopyrimidinyl, and imidazotriazinyl, each of which is optionally substituted with one or two members independently selected from chloro, fluoro, bromo, iodo, methyl, ethyl, propyl, and —$NH_2$. In some other embodiments, $R^4$ is pyrimidinyl or pyrazinyl, each of pyrimidinyl or pyrazinyl is substituted with at least one —$NH_2$. In certain other embodiments, $R^4$ is pyrimidinyl or pyrazinyl, each of which is substituted with two or three members independently selected from chloro, fluoro, bromo, iodo, methyl, ethyl, propyl, cyano, and —$NH_2$. In certain embodiments, $R^4$ is pyrimidinyl or pyrazinyl, each of which is substituted with at least two or three members, each of the members is independently selected from —$NH_2$, fluoromethyl, difluormethyl, trifluoromethyl, fluoroethyl, difluoroeethyl, trifluoroethyl, fluoropropyl, diluoropropyl, and trifluoropyl. In other embodiment, $R^4$ is selected from

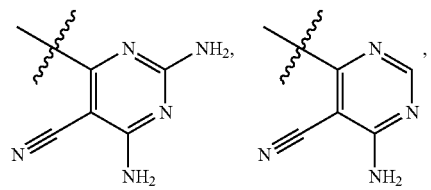

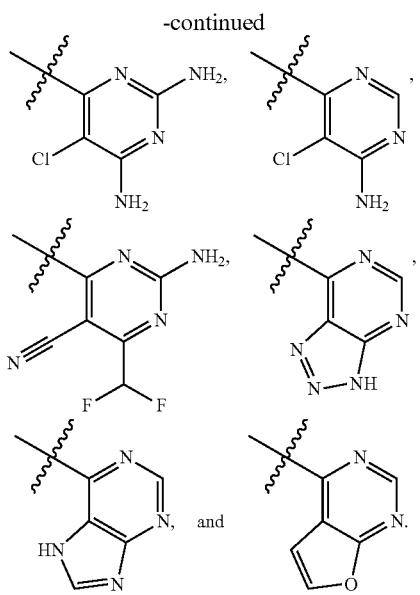

In one embodiment, p is 0. In some embodiments, p is 1 or 2. In the embodiment where p is 1. $R^{4a}$ moiety may be located on any position of the pyrimidinyl ring. When p is 2, both $R^{4a}$ substituents or moieties may be the same or different. In the embodiment where p is 2, both $R^{4a}$ substituents or moieties may be the same or different; each of the two $R^{4a}$ moieties may be located on any position of the pyrimidinyl ring. In the embodiment where p is 3, all $R^{4a}$ substituents may be the same or different, or two $R^{4a}$ may be the same and different from the third $R^{4a}$.

In the present application, each $R^{4a}$ is independently selected from halo, cyano, optionally substituted $C_{1-6}$ alkyl, and —$NH_2$. In one embodiment, each $R^{4a}$ is independently halo, cyano, $C_{1-4}$ alkyl, and —$NH_2$. In some embodiments, each $R^{4a}$ is independently selected from bromo, chloro, fluoro, iodo, cyano, methyl, ethyl, propyl, and —$NH_2$. In additional embodiments, each $R^{4a}$ is independently selected from bromo, chloro, fluoro, iodo, cyano, methyl, ethyl, propyl, fluoromethyl, difluoromethyl, trifluoromethyl, fluoroethyl, difluoroethyl, trifluoroethyl, fluoropropyl, difluoropropyl, trifluoropropyl, and —$NH_2$. In other embodiments, each $R^{4a}$ is independently selected fluoromethyl, difluoromethyl, trifluoromethyl, fluoroethyl, difluoroethyl, trifluoroethyl, fluoropropyl, difluoropropyl, trifluoropropyl, and —$NH_2$. Each and every variation of p and $R^{4a}$ may be combined with each and every variation of n, m, $R^1$, $R^2$, $R^3$, and $R^5$ as described above.

In the present application, $R^{1a}$, $R^{1b}$, $R^{1c}$, and $R^{1d}$ may be the same or different. Each $R^{1a}$, $R^{1b}$, $R^{1c}$, and $R^{1d}$ is independently selected from hydrogen, fluoro, chloro, bromo, and iodo. Also, $R^{2a}$ and $R^{2b}$ may be the same or different. Each $R^{2a}$ and $R^{2b}$ is independently selected from hydrogen, methyl, ethyl, and propyl. In one embodiment, $R^{1a}$ is chloro, and $R^{1b}$, $R^{1c}$, $R^{1d}$, $R^{2a}$, and $R^{2b}$ are hydrogen. In one other embodiment, $R^{1a}$ and $R^{1d}$ are chloro, and $R^{1b}$, $R^{1c}$, $R^{1d}$, $R^{2a}$, and $R^{2b}$ are hydrogen. In some other embodiments, $R^{1b}$ is chloro, $R^{1d}$ is fluoro, and $R^{1b}$, $R^{1c}$, $R^{2a}$, and $R^{2b}$ are hydrogen. In additional embodiments. $R^{2a}$ and $R^{2b}$ are hydrogen. In some additional embodiments, each $R^{1a}$, $R^{1b}$, $R^{1c}$, and $R^{1d}$ is independently selected from hydrogen, chloro, fluoro, bromo, iodo, and methyl.

In certain embodiments, W is CH or N. In certain other embodiments, W is CH. In yet other embodiments, W is N.

Each and every variation of W may be combined with each and every variation of n, m, $R^1$, $R^2$, $R^3$, $R^4$, and $R^5$ as described above.

The compounds of the present application may bear one or more chiral centers. The compounds bearing the chiral center have the same molecular formula and the same chemical name with different stereoisomer designations. For example, the below 3-(5-aminopyrazin-2-yl)-5-chloro-2-(1-((2,6-diamino-5-chloropyrimidin-4-yl)amino)ethyl)-8-fluoroquinazolin-4(3H)-one bearing one chiral center can be resolved into the (S) and (R) enantiomers, (S)-3-(5-aminopyrazin-2-yl)-5-chloro-2-(1-((2,6-diamino-5-chloropyrimidin-4-yl)amino)ethyl)-8-fluoroquinazolin-4(3H)-one and ((R)-3-(5-aminopyrazin-2-yl)-5-chloro-2-(1-((2,6-diamino-5-chloropyrimidin-4-yl)amino)ethyl)-8-fluoroquinazolin-4(3H)-one.

pounds are listed in Table 1a below. The compounds may be named using the nomenclature systems and symbols that are commonly recognized in the art of chemistry including, for example, ChemBioDraw Ultra 12.0, Chemical Abstract Service (CAS), and International Union of Pure and Applied Chemistry (IUPAC). For example, compound 2 in table 1 may be named as 2,4-diamino-6-[[(1S)-1-[3-(5-aminopyrazin-2-yl)-5-chloro-8-fluoro-4-oxo-quinazolin-2-yl]ethyl]amino]pyrimidine-5-carbonitrile or (S)-2,4-diamino-6-((1-(3-(5-aminopyrazin-2-yl)-5-chloro-8-fluoro-4-oxo-3,4-dihydroquinazolin-2-yl)ethyl)amino) pyrimidine-5-carbonitrile using IUPAC or ChemBioDraw Ultra 12.0, respectively.

TABLE 1

Representative Compounds

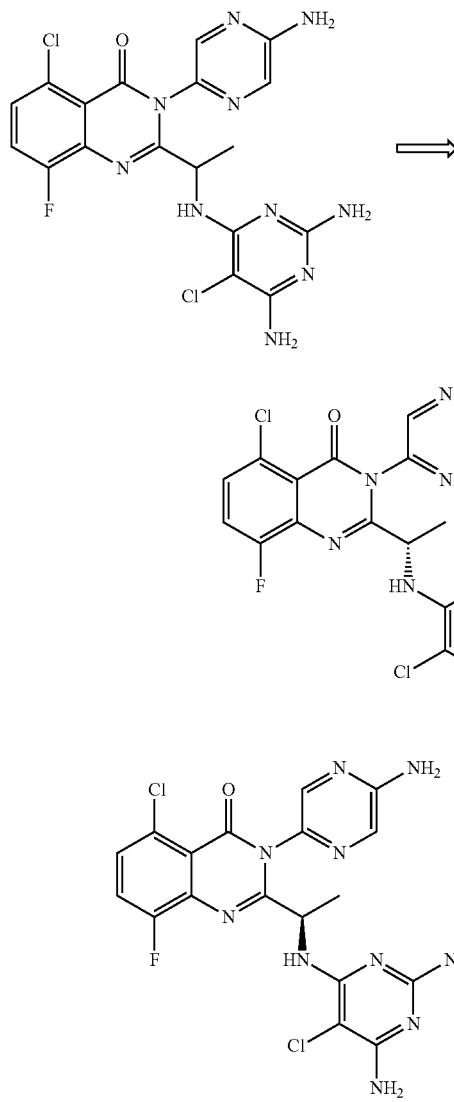

Representative compounds of the present application are listed in Table 1 below. Additional representative com- TABLE 1-continued Representative Compounds

| No. | Structure |
|---|---|
| 4 | (structure) |
| 5 | (structure) |
| 6 | (structure) |
| 7 | (structure) |
| 8 | (structure) |
| 9 | (structure) |
| 10 | (structure) |
| 11 | (structure) |

TABLE 1-continued
Representative Compounds
| No. | Structure |
|---|---|
| 12 | 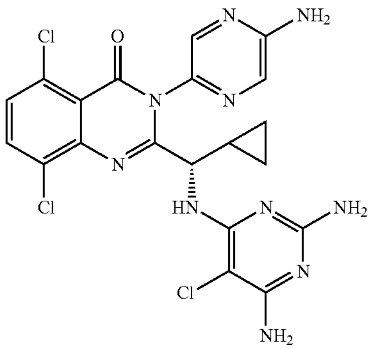 [SMILES: Nc1cnc(-n2c([C@@H](Nc3nc(N)nc(N)c3Cl)C3CC3)nc3c(Cl)ccc(Cl)c3c2=O)cn1] |
| 13 | 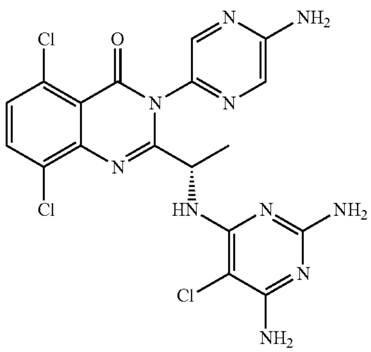 [SMILES: C[C@H](Nc1nc(N)nc(N)c1Cl)c1nc2c(Cl)ccc(Cl)c2c(=O)n1-c1cnc(N)cn1] |
TABLE 1a
Representative Compounds
| No. | Structure |
|---|---|
| 14 | 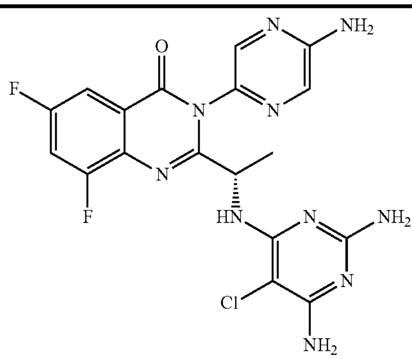 |
| 15 | 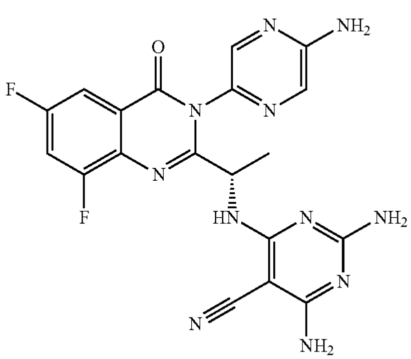 [SMILES: C[C@H](Nc1nc(N)nc(N)c1C#N)c1nc2c(F)cc(F)cc2c(=O)n1-c1cnc(N)cn1] |
TABLE 1a-continued
Representative Compounds
| No. | Structure |
|---|---|
| 16 | 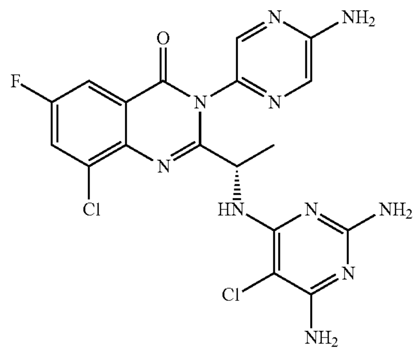 [SMILES: C[C@H](Nc1nc(N)nc(N)c1Cl)c1nc2c(Cl)cc(F)cc2c(=O)n1-c1cnc(N)cn1] |
| 17 | 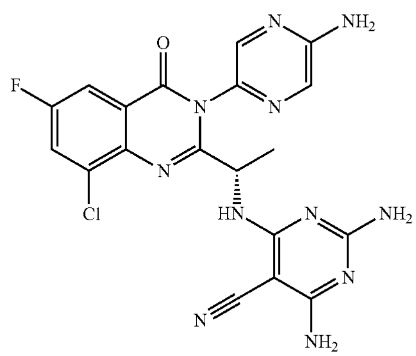 [SMILES: C[C@H](Nc1nc(N)nc(N)c1C#N)c1nc2c(Cl)cc(F)cc2c(=O)n1-c1cnc(N)cn1] |
| 18 | 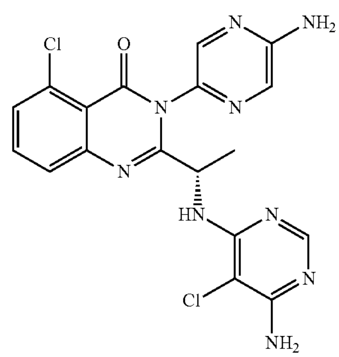 [SMILES: C[C@H](Nc1ncnc(N)c1Cl)c1nc2cccc(Cl)c2c(=O)n1-c1cnc(N)cn1] |
| 19 | 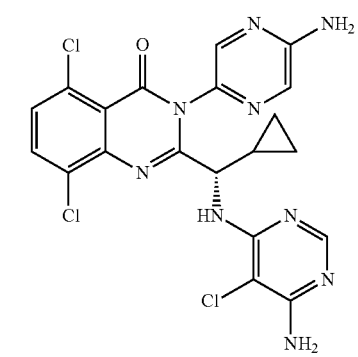 [SMILES: Nc1cnc(-n2c([C@@H](Nc3ncnc(N)c3Cl)C3CC3)nc3c(Cl)ccc(Cl)c3c2=O)cn1] |

TABLE 1a-continued

Representative Compounds

| No. | Structure |
|---|---|
| 20 | (structure) |
| 21 | (structure) |

The present application provides pharmaceutically acceptable salts, hydrates, solvates, isomers, tautomers, stereoisomers, enantiomers, racemates, atropisomers, polymorphs, prodrugs, or a mixture thereof, of the compounds described herein. In addition, the present application provides the compounds in which from 1 to n hydrogen atoms attached to a carbon atom may be replaced by a deuterium atom or D, in which n is the number of hydrogen atoms in the molecule. It is known that the deuterium atom is a non-radioactive isotope of the hydrogen atom. Such compounds may increase resistance to metabolism, and thus may be useful for increasing the half-life of the compounds of any of the formulae described herein or pharmaceutically acceptable salts, isomers, prodrugs, or solvates thereof, when administered to a mammal. See, e.g., Foster, "Deuterium Isotope Effects in Studies of Drug Metabolism", Trends Pharmacol. Sci., 5(12):524-527 (1984). Such compounds are synthesized by means well known in the art, for example by employing starting materials in which one or more hydrogen atoms have been replaced by deuterium.

The terms "a compound of the present application," "a compound described herein," "a compound of any of the formulae described herein," or variant thereof refer to a compound having the structure of any of the formulae (J), (I), (Ia), and (Ib). In some embodiments, compounds of the present application are Compounds 1-21 as described herein.

"Pharmaceutically acceptable" or "physiologically acceptable" refer to compounds, salts, compositions, dosage forms and other materials which are useful in preparing a pharmaceutical composition that is suitable for veterinary or human pharmaceutical use. "Pharmaceutically acceptable salts" or "physiologically acceptable salts" refer to salts of pharmaceutical compounds that retain the biological effectiveness and properties of the underlying compound, and which are not biologically or otherwise undesirable. There are acid addition salts and base addition salts. Pharmaceutically acceptable acid addition salts may be prepared from inorganic and organic acids. Acids and bases useful for reaction with an underlying compound to form pharmaceutically acceptable salts (acid addition or base addition salts respectively) are known to one of skill in the art. Similarly, methods of preparing pharmaceutically acceptable salts from an underlying compound (upon disclosure) are known to one of skill in the art and are disclosed in for example, Berge, at al. Journal of Pharmaceutical Science, Jan. 1977 vol. 66, No. 1, and other sources. If the compounds described herein are obtained as an acid addition salt, the free base can be obtained by basifying a solution of the acid salt. Conversely, if the product is a free base, an addition salt, particularly a pharmaceutically acceptable addition salt, may be produced by dissolving the free base in a suitable organic solvent and treating the solution with an acid, in accordance with conventional procedures for preparing acid addition salts from base compounds.

"Isomers" refers to compounds that have the same molecular formula. As used herein, the term isomers include double bond isomers, racemates, stereoisomers, enantiomers, diastereomers, and atropisomers. Single isomers, such as enantiomers or diastereomers, can be obtained by asymmetric synthesis or by resolution of a mixture of isomers. Resolution of a mixture of isomers (e.g. racemates) maybe accomplished, for example, by conventional methods such as crystallization in the presence of a resolving agent, or chromatography, using, for example a chiral high pressure liquid chromatography (HPLC) column. "Double bond isomers" refer to Z- and E-forms (or cis- and trans-forms) of the compounds with carbon-carbon double bonds.

"Atropisomers" refers to conformational stereoisomers which occur when rotation about a single bond in the molecule is prevented, or greatly hindered, as a result of steric interactions with other parts of the molecule and the substituents at both ends of the single bond are asymmetrical, i.e., they do not require a stereocenter. Where the rotational barrier about the single bond is high enough, and interconversion between conformations is slow enough, separation and isolation of the isomeric species may be permitted. Atropisomers may be separated by the methods well known in the art. Unless otherwise indicated, the description is intended to include individual atropisomers as well as mixtures. Also, as understood by those skilled in the art, the atropisomers may be represented by the same chemical name with different atropisomer designations.

"Racemates" refers to a mixture of enantiomers.

"Stereoisomers" or "stereoisomeric forms" refer to compounds that differ in the chirality of one or more stereocenters. Stereoisomers include enantiomers and diastereomers. The compounds may exist in stereoisomeric form if they possess one or more asymmetric centers or a double bond with asymmetric substitution and, therefore, can be produced as individual stereoisomers or as mixtures. Unless otherwise indicated, the description is intended to include individual stereoisomers as well as mixtures. The methods for the determination of stereochemistry and the separation of stereoisomers are well-known in the art (see, e.g., Chapter 4 of Advanced Organic Chemistry, 4th ed., J. March, John Wiley and Sons, New York, 1992).

"Tautomers" or "tautomeric formers" refer to alternate forms of a compound that differ in the position of a proton, such as enol-keto and imine-enamine tautomers, or heteroaryls such as pyrazoles, imidazoles, benzimidazoles, triazoles, and tetrazoles.

A "solvate" is formed by the interaction of a solvent and a compound. Solvates of salts of the compounds of any of the formulae described herein are also provided. Hydrates of the compounds of any of the formulae are also provided.

A "prodrug" is defined in the pharmaceutical field as a biologically inactive derivative of a drug that upon administration to the human body is converted to the biologically active parent drug according to some chemical or enzymatic pathway.

In any one of the foregoing embodiments, the compound described herein or a pharmaceutically acceptable salt thereof is an (S)-enantiomer. In any one of the foregoing embodiments, the compound described herein or a pharmaceutically acceptable salt thereof is an (R)-enantiomer. In any one of the foregoing embodiments, the compound described herein or a pharmaceutically acceptable salt thereof is an atropisomer.

The application also provides a composition containing a mixture of enantiomers of the compound or a pharmaceutically acceptable salt thereof. In one embodiment, the mixture is a racemic mixture. In other embodiments, the composition comprises the (S)-enantiomer of a compound in excess of over the corresponding the (R)-enantiomer of the compound. In some embodiments, the composition contains the (S)-enantiomer of the compound and is substantially free of its corresponding (R)-enantiomer. In certain embodiments, a composition substantially free of the (R)-enantiomer has less than or about 40%, 35%, 30%, 25%, 20%, 15%, 10%, 5%, 1%, 0.05%, or 0.01% of the (R)-enantiomer. In other embodiments, the composition containing the (S)-enantiomer of a compound or a pharmaceutically acceptable salt thereof, predominates over its corresponding (R)-enantiomer by a molar ratio of at least or about 9:1, at least or about 19:1, at least or about 40:1, at least or about 80:1, at least or about 160:1, or at least or about 320:1.

The composition containing a compound according to any of the formulae described herein or a pharmaceutically acceptable salt thereof, may also contain the compound in enantiomeric excess (e.e.). By way of example, a compound with 95% (S)-isomer and 5% (R)-isomer will have an e.e. of 90%. In some embodiments, the compound has an e.e. of at least or about 60%, 75%, 80%, 85%, 90%, 95%, 98% or 99%.

In any one of the foregoing embodiments, the compound or a pharmaceutically acceptable salt thereof, is an atropisomer. Another embodiment provides the composition containing a mixture of atropisomers of the compound or a pharmaceutically acceptable salt thereof. By way of example, a compound with 95% of one atropisomer and 5% of the other atropisomers. In some embodiments, a compound with about 90, 80, 70, 60, 50, 40, 30, 20, or 10% of one atropisomer and 10, 20, 30, 40, 50, 60, 70, 80, or 90%, respectively, of the other atropisomers.

The application also provides the free base forms of the compounds described herein. In certain embodiments, provided herein are the enantiomers, (R) or (S), of the compounds of the formulae described herein. In other embodiments, provided herein are the atropisomers of the compounds of the formulae described herein.

The application further provides compositions comprising the compounds described herein or a pharmaceutically acceptable salt, isomer, prodrug, or solvate thereof. The composition may include racemic mixtures, mixtures containing an enantiomeric excess of one enantiomer or single diastereomers or diastereomeric mixtures. All such isomeric forms of these compounds are expressly included herein, the same as if each and every isomeric form were specifically and individually listed.

In certain embodiments, provided herein are also polymorphs, such as crystalline and amorphous forms, of the compounds described herein. In some embodiments, provided are also chelates, non-covalent complexes, and mixtures thereof, of the compounds of the formula described herein or pharmaceutically acceptable salts, prodrugs, or solvates thereof. A "chelate" is formed by the coordination of a compound to a metal ion at two (or more) points. A "non-covalent complex" is formed by the interaction of a compound and another molecule wherein a covalent bond is not formed between the compound and the molecule. For example, complexation can occur through van der Waals interactions, hydrogen bonding, and electrostatic interactions (also called ionic bonding).

Therapeutic Uses of the Compounds

The compounds of the formulae described herein or a pharmaceutically acceptable salt, isomer, prodrug, or solvate thereof may be used for the treatment of diseases and/or conditions mediated by PI3K isoforms. In addition, the application provides the compounds for use in therapy. Also, provided herein are methods for inhibiting one or more PI3K isoforms. In one embodiment, provided are methods for inhibiting PI3Kδ activity using the compound described herein or a pharmaceutically acceptable salt, isomer, prodrug, or solvate thereof. In other embodiment, provided are methods for inhibiting PI3Kδ and/or PI3Kβ activities using the compound or a pharmaceutically acceptable salt, isomer, prodrug, or solvate thereof. The application further provides methods for use in such methods. The PI3K isoforms may be selectively or specifically inhibited. Additionally, the compounds may be used to inhibit PI3K activity therapeutically or prophylactically, such as PI3Kδ and/or PI3Kβ.

The compounds according to the present application may be used in combination with one or more additional therapeutic agents. The therapeutic agents may be in the forms of compounds, antibodies, polypeptides, or polynucleotides. The therapeutic agent includes, but is not limited to, a chemotherapeutic agent, an immunotherapeutic agent, a radiotherapeutic agent, an anti-neoplastic agent, an anti-cancer agent, an anti-proliferation agent, an anti-fibrotic agent, an anti-angiogenic agent, a therapeutic antibody, or any combination thereof. In one embodiment, the application provides a product comprising a compound described herein and an additional therapeutic agent as a combined preparation for simultaneous, separate or sequential use in therapy, e.g. a method of treating a disease, disorder, or condition that is mediated by PI3K isoforms.

Also, the therapeutic agents may be those that inhibit or modulate the activities of Bruton's tyrosine kinase, spleen tyrosine kinase, apoptosis signal-regulating kinase, Janus kinase, lysyl oxidase, lysyl oxidase-like proteins, matrix metallopeptidase, bromodomain-containing protein, adenosine A2B receptor, isocitrate dehydrogenase, serine/threonine kinase TPL2, discoidin domain receptor, serine/threonine-protein kinases, IKK, MEK, EGFR, histone deacetylase, protein kinase C, or any combination thereof. In certain embodiments, the therapeutic agent may be selected from a PI3K (including PI3Kγ, PI3Kδ, PI3Kβ, PI3Kα, and/or pan-PI3K) inhibitor, a JAK (Janus kinase, including JAK1, JAK2, and/or JAK3) inhibitor, a SYK (spleen tyrosine kinase) inhibitor, a BTK (Bruton's tyrosine kinase) inhibitor, an A2B (adenosine A2B receptor) inhibitor, an ACK (activated CDC kinase, including ACK1) inhibitor, an ASK (apoptosis signal-regulating kinase, including ASK1) inhibitor, Auroa kinase, a BRD (bromodomain-containing protein, including BRD4) inhibitor, a Bcl (B-cell CLL/lymphoma, including Bcl-1 and/or Bcl-2) inhibitor, a CAK (CDK-activating kinase) inhibitor, a CaMK (calmodulin-dependent protein kinases) inhibitor, a CDK (cyclin-dependent kinases, including CDK1, 2, 3, 4, and/or 6) inhibitor, a CK (casein kinase, including CK1 and/or CK2) inhibitor, a DDR (discoidin domain receptor, including DDR1 and/or DDR2) inhibitor, a EGFR inhibitor, a FXR (farnesoid x receptor) inhibitor, a FAK (focal adhesion kinase) inhibitor, a GSK (glycogen synthase kinase) inhibitor, a HDAC (histone deacetylase) inhibitor, an IDO (indoleamine 2,3-dioxygenase) inhibitor, an IDH (isocitrate dehydrogenase, including IDH1) inhibitor, an IKK (1-Kappa-B kinase) inhibitor, a KDM5 (lysine demethylase) inhibitor, a LCK (lymphocyte-specific protein tyrosine kinase) inhibitor, a LOX (lysyl oxidase) inhibitor, a LOXL (lysyl oxidase like protein, including LOXL1, LOXL2, LOXL3, LOXL4, and/or LOXL5) inhibitor, a MTH (mut T homolog) inhibitor, a MEK (mitogen-activated protein kinase kinase) inhibitor, a matrix metalloprotease (MMP, including MMP2 and/or MMP9) inhibitor, a mitogen-activated protein kinases (MAPK) inhibitor, a PD-1 (programmed cell death protein 1) inhibitor, a PD-L1 (programmed death-ligand 1) inhibitor, a PDGF (platelet-derived growth factor) inhibitor, a phosphorylase kinase (PK) inhibitor, a PLK (polo-like kinase, including PLK1, 2, 3) inhibitor, a protein kinase (PK, including protein kinase A, B, C) inhibitor, a STK (serine/threonine kinase) inhibitor, a STAT (signal transduction and transcription) inhibitor, a serine/threonine-protein kinase inhibitor, a TBK (tank-binding kinase) inhibitor, a TLR (toll-like receptor modulators, including TLR-1, TLR-2, TLR-3, TLR-4, TLR-5, TLR-6, TLR-7, TLR-8, TLR-9, TLR-10. TLR-11, TLR-12, and/or TLR-13) inhibitor, a TK (tyrosine kinase) inhibitor, a TPL2 (serine/threonine kinase) inhibitor, a NEK9 inhibitor, an Abl inhibitor, a p38 kinase inhibitor, a PYK inhibitor, a c-Kit inhibitor, a NPM-ALK inhibitor, a Flt-3 inhibitor, a c-Met inhibitor, a KDR inhibitor, a TIE-2 inhibitor, a VEGFR inhibitor, a SRC inhibitor, a HCK inhibitor, a LYN inhibitor, a FYN inhibitor, a YES inhibitor, a chemotherapeutic agent, an immunotherapeutic agent, a radiotherapeutic agent, an anti-neoplastic agent, an anti-cancer agent, an anti-proliferation agent, an anti-fibrotic agent, an anti-angiogenic agent, a therapeutic antibody, or any combination thereof. In some embodiments, the JAK inhibitor is N-(cyanomethyl)-4-[2-(4-morpholinoanilino)pyrimidin-4-yl]benzamide as named by ChemDraw (may also be referred to as CYT0387 or momelotinib) and may be synthesized by the methods described in U.S. Pat. No. 8,486,941. In certain embodiment, the SyK inhibitor is 6-(1H-indazol-6-yl)-N-(4-morpholinophenyl)imidazo[1,2-a]pyrazin-8-amine as named by ChemnDraw (may also be referred to as 6-(1H-indazol-6-yl)-N-[4-(morpholin-4-yl)phenyl]imidazo[1,2-a]pyrazin-8-amine) and may be synthesized by the methods described in U.S. Pat. No. 8,450,321. In other embodiments, the BTK inhibitor is (S)-6-amino-9-(1-(but-2-ynoyl)pyrrolidin-3-yl)-7-(4-phenoxyphenyl)-7H-purin-8(9H)-one as named by ChemDraw (may also be 6-amino-9-[(3R)-1-(2-butynoyl)-3-pyrrolidinyl]-7-(4-phenoxyphenyl)-7,9-dihydro-8H-purin-8-one) and may be synthesized by the methods in U.S. Pat. No. 8,557,803.

Chemotherapeutic agents may be categorized by their mechanism of action into, for example, the following groups: anti-metabolites/anti-cancer agents, such as pyrimidine analogs (floxuridine, capecitabine, and cytarabine); purine analogs, folate antagonists and related inhibitors, antiproliferative/antimitotic agents including natural products such as vinca alkaloid (vinblastine, vincristine) and microtubule such as taxane (paclitaxel, docetaxel), vinblastin, nocodazole, epothilones and navelbine, epidipodophyllotoxins (etoposide, teniposide); DNA damaging agents (actinomycin, amsacrine, busulfan, carboplatin, chlorambucil, cisplatin, cyclophosphamide, Cytoxan, dactinomycin, daunorubicin, doxorubicin, epirubicin, iphosphamide, melphalan, merchlorehtamine, mitomycin, mitoxantrone, nitrosourea, procarbazine, taxol, taxotere, teniposide, etoposide, triethylenethiophosphoramide); antibiotics such as dactinomycin (actinomycin D), daunorubicin, doxorubicin (adriamycin), idarubicin, anthracyclines, mitoxantrone, bleomycins, plicamycin (mithramycin) and mitomycin; enzymes (L-asparaginase which systemically metabolizes L-asparagine and deprives cells which do not have the capacity to synthesize their own asparagine); antiplatelet agents; antiproliferative/antimitotic alkylating agents such as nitrogen mustards cyclophosphamide and analogs, melphalan, chlorambucil), and (hexamethylmelamine and thiotepa), alkyl nitrosoureas (BCNU) and analogs, streptozocin), trazenes-dacarbazinine (DTIC); antiproliferative/antimitotic antimetabolites such as folic acid analogs (methotrexate); platinum coordination complexes (cisplatin, oxiloplatinim, carboplatin), procarbazine, hydroxyurea, mitotane, aminoglutethimide; hormones, hormone analogs (estrogen, tamoxifen, goserelin, bicalutamide, nilutamide) and aromatase inhibitors (letrozole, anastrozole); anticoagulants (heparin, synthetic heparin salts and other inhibitors of thrombin); fibrinolytic agents (such as tissue plasminogen activator, streptokinase and urokinase), aspirin, dipyridamole, ticlopidine, clopidogrel; antimigratory agents; antisecretory agents (breveldin); immunosuppressives tacrolimus sirolimus azathioprine, mycophenolate; compounds (TNP-470, genistein) and growth factor inhibitors (vascular endothelial growth factor inhibitors, fibroblast growth factor inhibitors); angiotensin receptor blocker, nitric oxide donors; anti-sense oligonucleotides; antibodies (trastuzumab, rituximab): cell cycle inhibitors and differentiation inducers (tretinoin); inhibitors, topoisomerase inhibitors (doxorubicin (adriamycin), daunorubicin, dactinomycin, eniposide, epirubicin, etoposide, idarubicin, irinotecan and mitoxantrone, topotecan, irinotecan, camptothesin), corticosteroids (cortisone, dexamethasone, hydrocortisone, methylpednisolone, prednisone, and prenisolone); growth factor signal transduction kinase inhibitors; dysfunction inducers, toxins such as Cholera toxin, ricin, *Pseudomonas exotoxin, Bordetella pertussis* adenylate cyclase toxin, or diphtheria toxin, and caspase activators; and chromatin.

As used herein the term "chemotherapeutic agent" or "chemotherapeutic" (or "chemotherapy." in the case of treatment with a chemotherapeutic agent) is meant to encompass any non-proteinaceous (i.e, non-peptidic) chemical compound useful in the treatment of cancer. Examples of chemotherapeutic agents include alkylating agents such as thiotepa and cyclophosphamide (CYTOXAN); alkyl sulfonates such as busulfan, improsulfan and piposulfan; aziridines such as bcnzodopa, carboquone, meturedopa, and uredopa; emylerumines and memylamelamines including alfretamine, triemylenemelamine, triethylenephosphoramide, triethylenethiophosphoramide and trimemylolomelamine; acetogenins (especially bullatacin and bullatacinone); a camptothecin (including synthetic analogue topotecan); bryostatin; callystatin; CC-1065 (including its adozelesin, carzelesin and bizelesin synthetic analogues); cryptophycins (articularly cryptophycin 1 and cryptophycin 8); dolastatin; duocarmycin (including the synthetic analogues, KW-2189 and CBI-TMI); eleutherobin; pancratistatin; a sarcodictyin; spongistatin; nitrogen mustards such as chlorambucil, chlornaphazine, cholophosphamide, estramustine, ifosfamide, mechlorethamine, mechlorethamine oxide hydrochloride, melphalan, novembichin, phenesterine, prednimustine, trofosfamide, uracil mustard; nitrosoureas such as carmustine, chlorozotocin, foremustine, lomustine, nimustine, ranimustine; antibiotics such as the enediyne antibiotics (e.g., calicheamicin, especially calicheamicin gammall and calicheamicin phill, see, e.g., Agnew, Chem. Intl. Ed. Engl, 33:183-186 (1994); dynemicin, including dynemicin A; bisphosphonates, such as clodronate; an esperamicin; as well as neocarzinostatin chromophore and related chromoprotein enediyne antibiotic chromomophores), aclacinomysins, actinomycin, authramycin, azascrine, bleomycins, cactinomycin, carabicin, carminomycin, carzinophilin, chromomycins, dactinomycin, daunorubicin, detorubicin, 6-diazo-5-oxo-L-norleucine, doxorubicin (including morpholino-doxorubicin, cyanomorpholino-doxorubicin, 2-pyrrolino-doxorubicin and deoxydoxorubicin), epirubicin, esorubicin, idarubicin, marcellomycin, mitomycins such as mitomycin C, mycophenolic acid, nogalamycin, olivomycins, peplomycin, potfiromycin, puromycin, quelamycin, rodorubicin, streptonigrin, streptozocin, tubercidin, ubenimex, zinostatin, zorubicin; anti-metabolites such as methotrexate and 5-fluorouracil (5-FU); folic acid analogues such as demopterin, methotrexate, pteropterin, trimetrexate; purine analogs such as fludarabinc, 6-mercaptopurine, thiamiprine, thioguanine; pyrimidine analogues such as ancitabine, azacitidine, 6-azauridine, carmofur, cytarabine, dideoxyuridine, doxifluridine, enocitabine, floxuridine; androgens such as calusterone, dromostanolone propionate, epitiostanol, mepitiostane, testolactone; anti-adrenals such as aminoglutethimide, mitotane, trilostane; folic acid replinisher such as frolinic acid; aceglatone; aldophosphamide glycoside; aminolevulinic acid; eniluracil; amsacrine; hestrabucil; bisantrene; edatraxate; defotamine; demecolcine; diaziquone; elformthine; elliptinium acetate; an epothilone; etoglucid; gallium nitrate; hydroxyurea; lentinan; leucovorin; lonidamine; maytansinoids such as maytansine and ansamitocins; mitoguazone; mitoxantrone; mopidamol; nitracrine; pentostatin; phenamet; pirarubicin; losoxantrone; fluoropyrimidine; folinic acid; podophyllinic acid; 2-ethylhydrazide; procarbazine; PSK(r); razoxane; rhizoxin; sizofiran; spirogermanium; tenuazonic acid; triaziquone; 2,2',2"-tricUorotriemylaminc; trichothecenes (especially T-2 toxin, verracurin A, roridin A and anguidine); urethane; vindesine; dacarbazine: mannomustine; mitobronitol; mitolactol; pipobroman; gacytosine; arabinoside ("Ara-C"); cyclophosphamide; thiopeta; taxoids, e.g., paclitaxel (TAXOL(r) and docetaxel (TAXOTERE(r)); chlorambucil; gemcitabine (Gemzar(r)); 6-thioguanine; mercaptopurine; methotrexate; platinum analogs such as cisplatin and carboplatin; vinblastine; platinum; etoposide (VP-16); ifosfamide; mitroxantrone; vancristine; vinorelbine (Navelbine(r)); novantrone; teniposide; edatrexate; daunomycin; aminopterin; xeoloda; ibandronate; CPT-11; topoisomerase inhibitor RFS 2000; difluoromethylornithine (DMFO); retinoids such as retinoic acid; capecitabine; FOLFIRI (fluorouracil, leucovorin, and irinotecan) and pharmaceutically acceptable salts, acids or derivatives of any of the above. One or more chemotherapeutic agent are used or included in the present application.

Also included in the definition of "chemotherapeutic agent" are anti-hormonal agents that act to regulate or inhibit hormone action on tumors such as anti-estrogens and selective estrogen receptor modulators (SERMs), including, for example, tamoxifen (including Nolvadex™), raloxifene, droloxifene, 4-hydroxytamoxifen, trioxifene, keoxifene, LY 17018, onapristone, and toremifene (Fareston(r)); inhibitors of the enzyme aromatase, which regulates estrogen production in the adrenal glands, such as, for example, 4(5)-imidazoles, aminoglutethimide, megestrol acetate (Megace (r)), exemestane, formestane, fadrozole, vorozole (Rivisor (r)), letrozole (Femara(r)), and anastrozole (Arimidex(r)); and anti-androgens such as flutamide, nilutamide, bicalutamide, leuprohde, and goserelin; and pharmaceutically acceptable salts, acids or derivatives of any of the above.

The anti-angiogenic agents include, but are not limited to, retinoid acid and derivatives thereof, 2-methoxyestradiol, ANGIOSTATIN(r), ENDOSTATIN(r), suramin, squalamine, tissue inhibitor of metalloproteinase-1, tissue inhibitor of metalloproternase-2, plasminogen activator inhibitor-1, plasminogen activator inbibitor-2, cartilage-derived inhibitor, paclitaxel (nab-paclitaxel), platelet factor 4, protamine sulphate (clupeine), sulphated chitin derivatives (prepared from queen crab shells), sulphated polysaccharide peptidoglycan complex (sp-pg), staurosporine, modulators of matrix metabolism, including for example, proline analogs ((1-azetidine-2-carboxylic acid (LACA), cishydroxyproline, d,I-3,4-dehydroproline, thiaproline, .alpha.-dipyridyl, beta-aminopropionitrile fumarate, 4-propyl-5-(4-pyridinyl)-2 (3h)-oxazolone; methotrexate, mitoxantrone, heparin, interferons, 2 macroglobulin-serum, chimp-3, chymostatin, beta-cyclodextrin tetradecasulfate, eponemycin; fumagillin, gold sodium thiomalate, d-penicillamine (CDPT), beta-1-anticollagenase-serum, alpba-2-antiplasmin, bisantrene, lobenzarit disodium, n-2-carboxyphenyl-4-chloroanthronilic acid disoditun or "CCA", thalidomide: angiostatic steroid, cargboxynaminolmidazole; metalloproteinase inhibitors such as BB94. Other anti-angiogenesis agents include antibodies, preferably monoclonal antibodies against these angiogenic growth factors: beta-FGF, alpha-FGF, FGF-5, VEGF isoforms, VEGF-C, HGFiSF and Ang-1/Ang-2. See Ferrara N, and Alitalo, K. "Clinical application of angiogenic growth factors and their inhibitors" (1999) Nature Medicine 5:1359-1364.

The anti-fibrotic agents include, but are not limited to, the compounds such as beta-amninoproprionitrile (BAPN), as well as the compounds disclosed in U.S. Pat. No. 4,965,288 to Palfreyman, et al., issued Oct. 23, 1990, entitled "Inhibitors of lysyl oxidase," relating to inhibitors of lysyl oxidase and their use in the treatment of diseases and conditions associated with the abnormal deposition of collagen; U.S. Pat. No. 4,997,854 to Kagan, et al., issued Mar. 5, 1991, entitled "Anti-fibrotic agents and methods for inhibiting the activity of lysyl oxidase in situ using adjacently positioned diamine analogue substrate," relating to compounds which inhibit LOX for the treatment of various pathological fibrotic states, which are herein incorporated by reference. Further exemplary inhibitors are described in U.S. Pat. No. 4,943,593 to Palfreyman, et al., issued Jul. 24, 1990, entitled "Inhibitors of lysyl oxidase," relating to compounds such as 2-isobutyl-3-fluoro-, chloro-, or bromo-allylamine; as well as, e.g., U.S. Pat. Nos. 5,021,456; 5,5059,714; 5,120,764; 5,182,297; 5,252,608 (relating to 2-(1-naphthyloxymemyl)-3-fluoroallylamine); and U.S. Patent Application No. 2004/0248871, which are herein incorporated by reference. Exemplary anti-fibrotic agents also include the primary amines reacting with the carbonyl group of the active site of the lysyl oxidases, and more particularly those which produce, after binding with the carbonyl, a product stabilized by resonance, such as the following primary amines: emylenemamine, hydrazine, phenylhydrazine, and their derivatives, semicarbazide, and urea derivatives, aminonitriles, such as beta-aminopropionitrile (BAPN), or 2-nitroethylamine, unsaturated or saturated haloamines, such as 2-bromo-ethylamine, 2-chloroethylamine, 2-trifluoroethylamine, 3-bromopropylamine, p-halobenzylamines, selenohomocysteine lactone. Also, the anti-fibrotic agents are copper chelating agents, penetrating or not penetrating the cells. Exemplary compounds include indirect inhibitors such compounds blocking the aldehyde derivatives originating from the oxidative deamination of the lysyl and hydroxylysyl residues by the lysyl oxidases, such as the thiolamines, in particular D-penicillamine, or its analogues such as 2-amino-5-mercapto-5-methylhexanoic acid, D-2-amino-3-methyl-3-((2-acetamidoethyl)dithio)butanoic acid, p-2-amino-3-methyl-3-((2-aminoethyl)dithio)butanoic acid, sodium-4-((p-1-dimethyl-2-amino-2-carboxyethyl)dithio)butane sulphurate, 2-acetamidoethyl-2-acetamidocthanethiol sulphanate, sodium-4-mercaptobutanesulphinate trihydrate.

The immunotherapeutic agents include and are not limited to therapeutic antibodies suitable for treating patients; such as abagovomab, adecatumumab, afutuzumab, alemtuzumab, altumomab, amatuximab, anatumomab, arcitumomab, bavituximab, bectumomab, bevacizumab, bivatuzumab, blinatumomab, brentuximab, cantuzumab, catumaxomab, cetuximab, citatuzumab, cixutumumab, clivatuzumab, conatumumab, daratumumab, drozitumab, duligotumab, dusigitumab, detumomab, dacetuzumab, dalotuzumab, ecromeximab, elotuzumab, ensituximab, ertumaxomab, etaracizumab, farietuzumab, ficlatuzumab, figitumumab, flanvotumab, futuximab, ganitumab, gemtuzumab, girentuximab, glembatumumab, ibritumomab, igovomab, imgatuzumab, indatuximab, inotuzumab, intetumumab, ipilimumab, iratumumab, labetuzumab, lexatumumab, lintuzumab, lorvotuzumab, lucaturnumab, mapatumumab, matuzumab, milatuzumab, minretumomab, mitumomab, moxetumomab, narnatunab, naptumomab, necitumumab, nimotuzumnab, nofetumomabn, ocaratuzumab, ofatumumab, olaratumab, onartuzumab, oportuzumab, oregovomab, panitumumab, parsatuzumab, patritumab, pemtumomab, pertuzumab, pintumomab, pritumumab, racotumomab, radretumab, rilotumumab, rituximab, robatumumab, satumomab, sibrotuzumab, siltuximab, simtuzumab, solitomab, tacatuzumab, taplitumomab, tenatumomab, teprotumnumab, tigatuzumab, tositumomab, trastuzumab, tucotuzumab, ublituximab, veltuzumab, vorsetuzumab, votumumab, zalutumumab, obinutuzumab, CC49 and 3F8. The exemplified therapeutic antibodies may be further labeled or combined with a radioisotope particle, such as indium In 111, yttrium Y 90, iodine I-131.

The application also provides method for treating a subject who is undergoing one or more standard therapies, such as chemotherapy, radiotherapy, immunotherapy, surgery, or combination thereof. Accordingly, one or more therapeutic agent or inhibitors may be administered before, during, or after administration of chemotherapy, radiotherapy, immunotherapy, surgery or combination thereof.

Other examples of chemotherapy treatments (including standard or experimental chemotherapies) are described below. In addition, treatment of certain lymphomas is reviewed in Cheson, B. D., Leonard. J. P., "Monoclonal Antibody Therapy for B-Cell Non-Hodgkin's Lymphoma" *The New England Journal of Medicine* 2008, 359(6), p. 613-626; and Wierda, W. G., "Current and Investigational Therapies for Patients with CLL" *Hematology* 2006, p. 285-294. Lymphoma incidence patterns in the United States is profiled in Morton, L. M., et al. "Lymphoma Incidence Patterns by WHO Subtype in the United States, 1992-2001" *Blood* 2006, 107(1), p. 265-276.

Examples of immunotherapeutic agents include, but are not limited to, rituximab (such as Rituxan), alemtuzumab (such as Campath, MabCampath), anti-CD19 antibodies, anti-CD20 antibodies, anti-MN-14 antibodies, anti-TRAIL, Anti-TRAIL DR4 and DR5 antibodies, anti-CD74 antibodies, apolizumab, bevacizumab, CHIR-12.12, epratuzumab (hLL2-anti-CD22 humanized antibody), galiximab, ha20, ibritumomab tiuxetan, lumiliximab, milatuzumab, ofatumumab, PRO131921, SGN-40, WT-1 analog peptide vaccine, WT1 126-134 peptide vaccine, tositumomab, autologous human tumor-derived HSPPC-96, and veltuzumab. Additional immunotherapy agents includes using cancer vaccines based upon the genetic makeup of an individual patient's tumor, such as lymphoma vaccine example is GTOP-99 (MyVax®).

Examples of chemotherapy agents include aldesleukin, alvocidib, antineoplaston AS2-1, antineoplaston A10, anti-thymocyte globulin, amifostine trihydrate, aminocamptothecin, arsenic trioxide, beta alethine, Bcl-2 family protein inhibitor ABT-263, ABT-199, BMS-345541, bortezomib (Velcade®), bryostatin 1, busulfan, carboplatin, campath-1H, CC-5103, carmustine, caspofungin acetate, clofarabine, cisplatin, Cladribine (Leustarin), Chlorambucil (Leukeran), Curcumin, cyclosporine, Cyclophosphamide (Cyloxan, Endoxan, Endoxana, Cyclostin), cytarabine, denileukin diftitox, dexamethasone, DT PACE, docetaxel, dolastatin 10, Doxorubicin (Adriamycin®, Adriblastine), doxorubicin hydrochloride, enzastaurin, epoetin alfa, etoposide, Everolimus (RAD001), fenretinide, filgrastim, melphalan, mesna, Flavopiridol, Fludarabine (Fludara), Geldanamycin (17-AAG), ifosfamide, irinotecan hydrochloride, ixabepilone, Lenalidomide (Revlimid®, CC-5013), lymphokine-activated killer cells, melphalan, methotrexate, mitoxantrone hydrochloride, motexafin gadolinium, mycophenolate mofetil, nelarabine, oblimersen (Genasense) Obatoclax (GX15-070), oblimersen, octreotide acetate, omega-3 fatty acids, oxaliplatin, paclitaxel, PD0332991, PEGylated liposomal doxorubicin hydrochloride, pegfilgrastim, Pentstatin (Nipent), perifosine, Prednisolone, Prednisone, R-roscovitine (Selicilib, CYC202), recombinant interferon alfa, recombinant interleukin-12, recombinant interleukin-11, recombinant flt3 ligand, recombinant human thrombopoietin, rituximab, sargramostim, sildenafil citrate, simvastatin, sirolimus, Styryl sulphones, tacrolimus, tanespimycin, Temsirolimus (CCl-779), Thalidomide, therapeutic allogeneic lymphocytes, thiotepa, tipifarnib, Velcade® (bortezomib or PS-341), Vincristine (Oncovin), vincristine sulfate, vinorelbine ditartrate, Vorinostat (SAHA), vorinostat, and FR (fludarabine, rituximab), CHOP (cyclophosphamide, doxorubicin, vincristine, prednisone), CVP (cyclophosphamide, vincristine and prednisone), FCM (fludarabine, cyclophosphamide, mitoxantrone), FCR (fludarabine, cyclophosphamide, rituximab), hyperCVAD (hyperfractionated cyclophosphamide, vincristine, doxorubicin, dexamethasone, methotrexate, cytarabine), ICE (iphosphamide, carboplatin and etoposide), MCP (mitoxantrone, chlorambucil, and prednisolone), R-CHOP (rituximab plus CHOP), R-CVP (rituximab plus CVP), R-FCM (rituximab plus FCM), R-ICE (rituximab-ICE), and R-MCP (R-MCP).

The therapeutic treatments can be supplemented or combined with any of the abovementioned therapies with stem cell transplantation or treatment. One example of modified approach is radioimmunotherapy, wherein a monoclonal antibody is combined with a radioisotope particle, such as indium In 111, yttrium Y 90, iodine I-131. Examples of combination therapies include, but are not limited to, Iodine-131 tositumomab (Bexxar®), Yttrium-90 ibrituinomab tiuxetan (Zevalin®), Bexxar® with CHOP.

Other therapeutic procedures include peripheral blood stem cell transplantation, autologous hematopoietic stem cell transplantation, autologous bone marrow transplantation, antibody therapy, biological therapy, enzyme inhibitor therapy, total body irradiation, infusion of stem cells, bone marrow ablation with stem cell support, in vitro-treated peripheral blood stem cell transplantation, umbilical cord blood transplantation, immunoenzyme technique, pharmacological study, low-LET cobalt-60 gamma ray therapy, bleomycin, conventional surgery, radiation therapy, and nonmyeloablative allogeneic hematopoietic stem cell transplantation.

In some embodiments, the methods include administering a compound of the formula described herein or a pharmaceutically acceptable salt, isomer, prodrug, or solvate thereof, in a therapeutically effective amount to a human in need thereof. The method can be employed to treat a patient who has or is believed to have a disease or condition whose symptoms or pathology is mediated by expression or activity of PI3Kβ and/or PI3Kδ. The patient may be a mammal or a human. In certain embodiment, the patient may be a human.

"Treatment" or "treating" is an approach for obtaining beneficial or desired results including clinical results. Beneficial or desired clinical results may include one or more of the following: a) inhibiting the disease or condition (e.g., decreasing one or more symptoms resulting from the disease or condition, and/or diminishing the extent of the disease or condition); b) slowing or arresting the development of one or more clinical symptoms associated with the disease or condition (e.g., stabilizing the disease or condition, preventing or delaying the worsening or progression of the disease or condition, and/or preventing or delaying the spread (e.g., metastasis) of the disease or condition); and/or c) relieving the disease, that is, causing the regression of clinical symptoms (e.g., ameliorating the disease state, providing partial or total remission of the disease or condition, enhancing the effect of another medication, delaying the progression of the disease, increasing the quality of life, and/or prolonging survival.

"Prevention" or "preventing" mean any treatment of a disease or condition that causes the clinical symptoms of the disease or condition not to develop. Compounds may, in some embodiments, be administered to a subject (including a human) who is at risk or has a family history of the disease or condition.

"Subject" or "patient" refer to an animal, such as a mammal (including a human), that has been or will be the object of treatment, observation or experiment. The methods described herein may be useful in human therapy and/or veterinary applications. In some embodiments, the subject is a mammal. In one embodiment, the subject is a human. "Human in need thereof" refers to a human who may have or is suspect to have diseases, or disorders, or conditions that would benefit from certain treatment; for example, being treated with the PI3K inhibitor of the compounds according to the present application. In certain embodiments, the subject may be a human who (i) has not received any treatment including chemotherapy treatment, (ii) is substantially refractory to at least one chemotherapy treatment, (iii) is in relapse after treatment with chemotherapy, or both (i) and (ii). In some of embodiments, the subject is refractory to at least one, at least two, at least three, or at least four chemotherapy treatments (including standard or experimental chemotherapies).

The terms "therapeutically effective amount" or "effective amount" of a compound of the present application or a pharmaceutically acceptable salt, isomers, prodrug, or solvate thereof, mean an amount sufficient to effect treatment when administered to a subject, to provide a therapeutic benefit such as amelioration of symptoms or slowing of disease progression. For example, a therapeutically effective amount may be an amount sufficient to decrease a symptom of a disease or condition responsive to inhibition of PI3Kδ and PI3Kβ activity. The therapeutically effective amount may vary depending on the subject, and disease or condition being treated, the weight and age of the subject, the severity of the disease or condition, and the manner of administering, which can readily be determined by one or ordinary skill in the art.

In addition to the therapeutic uses, the compounds described herein have the selectivity or selective inhibition to certain PI3K isoforms. In one embodiment, the compounds have selectivity to PI3Kβ. In some embodiments, the compounds have selectivity to PI3Kδ. In yet other embodiments, the compounds have selectivity to PI3Kβ and PI3Kδ. The selectivity to PI3K isoforms may be determined by measuring the compound's activity in inhibiting certain PI3K isoforms using the assay described in the example below or the methods commonly used. It is understood that the conditions (e.g. the reagent concentration or the incubation temperature) may be varied and the results of the assay may vary. In some instances, the value may vary within a range of one to three-folds.

The term "inhibition" indicates a decrease in the baseline activity of a biological activity or process. The term "inhibition of activity of PI3K isoforms" or variants thereof refer to a decrease in activity in any PI3K isoform (e.g., alpha, beta, gamma, or delta) as a direct or indirect response to the presence of a compound of any of the formula described herein relative to the activity of PI3K isoform in the absence of such compound. "Inhibition of PI3Kδ and/or PI3Kβ activities" or variants thereof refer to a decrease in PI3Kδ and/or PI3Kβ activities as a direct or indirect response to the presence of the compounds described herein, relative to the activities of PI3Kδ and/or PI3Kβ in the absence of such compound. In some embodiments, the inhibition of PI3K isoform activities may be compared in the same subject prior to treatment, or other subjects not receiving the treatment.

Without being bound to any theory, the decrease in the activity of PI3K may be due to the direct interaction of the compound with PI3K, or due to the interaction of the compounds described herein with one or more other factors that affect PI3K activity. For example, the presence of the compounds may decrease the activities of PI3Kδ and/or PI3Kβ by directly binding to PI3Kδ and/or PI3Kβ, by causing (directly or indirectly) another factor to decrease PI3Kδ and/or PI3Kβ activities, or by (directly or indirectly) decreasing the amount of PI3Kδ and/or PI3Kβ present in the cell or organism.

The term "PI3K inhibitor" or variant thereof refers to a compound that inhibits the activity of PI3K. The term "PI3K isoform selective inhibitor" or variant thereof refers to a compound that inhibits the activity of one or more PI3K isoforms more effectively than the other remaining PI3K isoforms. By way of example, the term "PI3Kβ selective inhibitor" generally refers to a compound that inhibits the activity of the PI3Kβ isoform more effectively than other isoforms of the PI3K family, and the term "PI3K δ selective inhibitor" generally refers to a compound that inhibits the activity of the PI3Kδ isoform more effectively than other isoforms of the PI3K family. The term "dual PI3Kδ/β selective inhibitor" generally refers to a compound that inhibits the activity of both PI3Kδ and PI3Kβ isoforms more effectively than other isoforms of the PI3K family (e.g., PI3K α or γ).

The relative efficacies of compounds as inhibitors of an enzyme activity (or other biological activity) can be established by determining the concentrations at which each compound inhibits the activity to a predefined extent and then comparing the results. In one embodiment, the efficacy of a compound as an inhibitor of one or more PI3K isoforms can be measured by the compound concentration that inhibits 50% of the activity in a biochemical assay. i.e., the 50% inhibitory concentration or "ICs)". The determination of $IC_{50}$ values can be accomplished using conventional techniques known in the art, including the techniques described in the Examples below. In general, an $IC_{50}$ can be determined by measuring the activity of a given enzyme in the presence of a range of concentrations of the compound under the study. The experimentally obtained values of enzyme activity may then be plotted against the compound concentrations used. The concentration of the inhibitor that shows 50% enzyme activity (as compared to the activity in the absence of any inhibitor) is taken as the $IC_{50}$ value. Analogously, other inhibitory concentrations can be defined through appropriate determinations of activity. For example, in some settings it may be desirable to establish a 90% inhibitory concentration, i.e., $IC_{90}$.

According to the present application, a PI3Kβ selective inhibitor is a compound that exhibits a 50% inhibitory concentration ($IC_{50}$) with respect to PI3Kβ that is at least 10-fold, at least 20-fold, at least 30-fold, at least 50-fold, at least 100-fold, at least 200-fold, or at least 500-fold lower than the $IC_{50}$ with respect to either PI3Kα or PI3Kγ or both PI3Kα and PI3Kγ. In addition, a PI3Kδ/β selective inhibitor is a compound that exhibits a 50% inhibitory concentration ($IC_{50}$) with respect to PI3 KB and PI3Kδ that is at least 10-fold, at least 20-fold, at least 30-fold, at least 50-fold, at least 75-fold, at least 100-fold, at least 200-fold, and at least 500-fold lower than the $IC_{50}$ with respect to either PI3Kα or PI3Kγ. The dual PI3Kδ/β selective inhibitor may have the same or similar $IC_{50}$ to both PI3Kδ and PI3Kβ or may have different $IC_{50}$ to either PI3Kδ or PI3Kβ. As used herein, the term "potency," "potent," or variants thereof refer to the compound exhibiting an $IC_{50}$ value that is less than 100 nM. When comparing two compounds, the compound that exhibits a lower $IC_{50}$ value is referred to as a more potent inhibitor.

The compounds of the present application exhibit unexpected selectivity to PI3Kβ. As shown in the example, certain compounds in Table 1 exhibit low $IC_{50}$ values (e.g. 1 to 100 nM) to both PI3Kβ and PI3Kδ. Certain compounds in Table 1a also exhibited such selectivity to PI3K isoforms. Also, certain compounds of formula (I) exhibited at least between 10-fold to 400-fold lower $IC_{50}$ values for PI3Kβ than PI3Kγ, suggesting the compounds exhibit more selectivity to PI3Kβ compared to PI3Kγ (i.e., inhibits the activity of the PI3Kβ isoform more effectively than the PI3Kγ isoform as shown by the PI3Kγ/PI3Kβ ratio). Moreover, the compounds described herein exhibit selectivity to both PI3Kβ and PI3Kδ. The compound (S)-2,4-diamino-6-((1-(5-chloro-4-oxo-3-phenyl-3,4-dihydroquinazolin-2-yl)ethyl)amino)pyrimidine-5-carbonitrile, described in U.S. Provisional Application No. 61/745,437, exhibited less selectivity to PI3Kγ (e.g. the PI3Kγ/PI3Kβ ratio is less than 1-fold). The results of the present application suggest that the compounds described herein are dual selective inhibitors of PI3Kδ and PI3Kβ and exhibit more selectivity to PI3Kβ compared to PI3Kγ. Each of the patents and the patent applications described in the present application are incorporated herein by the entirety.

The methods described herein may be applied to cell populations in vivo or ex vivo. "In vivo" means within a living individual, as within an animal or human. In this context, the methods described herein may be used therapeutically in an individual. "Ex vivo" means outside of a living individual. Examples of ex vivo cell populations include in vitro cell cultures and biological samples including fluid or tissue samples obtained from individuals. Such samples may be obtained by methods well known in the art. Exemplary biological fluid samples include blood, cerebrospinal fluid, urine, and saliva. Exemplary tissue samples include tumors and biopsies thereof. In this context, the compounds may be used for a variety of purposes, including therapeutic and experimental purposes. For example, it may be used ex vivo to determine the optimal schedule and/or dosing of administration of a PI3K selective inhibitor for a given indication, cell type, individual, and other parameters. Information gleaned from such use may be used for experimental purposes or in the clinic to set protocols for in vive treatment. Other ex vivo uses for which the invention may be suited are described below or will become apparent to those skilled in the art. The compounds of the formula described herein or a pharmaceutically acceptable salt, pro-drug, or solvate thereof, may be further characterized to examine the safety or tolerance dosage in human or non-human subjects. Such properties may be examined using commonly known methods to those skilled in the art.

Compared to other PI3K isoforms, PI3Kδ is generally expressed in hematopoietic cells. Also, PI3Kβ is generally mis-regulated in certain cancer cells. Aberrant proliferation of cells often interferes with normal tissue function, which may result in abnormal cellular response such as immunity, inflammation, and/or apoptosis. The selective inhibitors to PI3Kδ and/or PI3Kβ are useful in treating, inhibiting, or preventing aberrant proliferation of cancerous and/or hematopoictic cells and ameliorating the symptoms and secondary conditions.

The compounds described herein may be used to treat subjects having various disease states, disorders, and conditions (also collectively referred to as "indications") associated with PI3K isoforms or their activities. As used herein, the terms "diseases." "disorders," "conditions" are used interchangeably. Such indications may include, for example, cancer, including hematologic malignancies (e.g. leukemias and lymphomas, myeloproliferative disorders, myelodysplastic syndromes, plasma cell neoplasms) and solid tumors, inflammation, fibrosis, allergic conditions (including hypersensitivity), cardiovascular diseases, neurodegenerative diseases, renal disorders, viral infections, obesity, and autoimmune diseases.

In other embodiments, the compounds described herein may be used to treat cancers that are mediated by, dependent on, or associated with PI3K activity. In certain embodiments, the disease or condition is an autoimmune disease, an inflammatory disease, or a cancer. In some embodiments, the disease or condition is chosen from rheumatoid arthritis, osteoarthritis, atherosclerosis, psoriasis, systemic lupus erythematosus, multiple sclerosis, inflammatory bowel disease, asthma, chronic obstructive airways disease, pneumonitis, dermatitis, alopecia, nephritis, vasculitis, atherosclerosis, Alzheimer's disease, hepatitis, primary biliary cirrhosis, sclerosing cholangitis, diabetes (including type I diabetes), acute rejection of transplanted organs, lymphomas, multiple myelomas, leukemias, neoplasms and solid tumors.

In other embodiments, the disease is a solid tumor. By way of examples, the solid tumor includes but is not limited to pancreatic cancer, bladder cancer, colorectal cancer, breast cancer, prostate cancer, renal cancer, hepatocellular cancer, lung cancer, ovarian cancer, cervical cancer, rectum cancer, liver cancer, kidney cancer, stomach cancer, skin cancer, gastric cancer, esophageal cancer, head and neck cancer, melanoma, neuroendocrine cancers, CNS cancers (e.g., neuroblastoma), brain tumors (e.g., glioma, anaplastic oligodendroglioma, adult glioblastoma multiforme, and adult anaplastic astrocytoma), bone cancer, or soft tissue sarcoma. In some embodiments, the solid tumor is non-small cell lung cancer, small-cell lung cancer, colon cancer, CNS cancer, melanoma, ovarian cancer, renal cancer, pancreatic cancer, prostate cancer, or breast cancer.

The present application also provides a method for treating a human in need thereof, who has or is suspected of having a disease or condition responsive or believed to be responsive to the inhibition of PI3Kδ and/or PI3Kβ activity by administering to the subject a compound of the formulae described herein or a pharmaceutically acceptable salt, enantiomer, atropisomer, tautomer, prodrug, or solvate thereof.

Additionally, the application provides a method of inhibiting kinase activity of a PI3Kδ and/or PI3Kβ polypeptides by contacting the polypeptides with a compound of the formulae described herein or a pharmaceutically acceptable salt, isomer, prodrug, solvate, or a mixture thereof.

Moreover, the application provides a method of decreasing cell viability, increasing cell death or apoptosis, increasing interference with PI3K signaling pathways (including AKT, S6RP, ERK phosphorylation), and/or reduction in chemokine production with an effective amount of a compound of any of the formulae described herein or a pharmaceutically acceptable salt, isomer, prodrug, solvate, or a mixture thereof.

The application further provides a method of disrupting leukocyte function comprising contacting the leukocytes with an effective amount of a compound of any of the formulae described herein or a pharmaceutically acceptable salt, isomer, prodrug, solvate, or a mixture thereof in a human in need thereof.

Provided is also a method of inhibiting growth or proliferation of cancer cells comprising contacting the cancer cells with an effective amount of a compound of the formulae described herein or a pharmaceutically acceptable salt, isomer, prodrug, solvate, or a mixture thereof.

Kits

Provided herein are also kits that include a compound of the formulae of the present application or a pharmaceutically acceptable salt, isomer, prodrug, or solvate thereof, and suitable packaging. In one embodiment, a kit further includes instructions for use. In one aspect, a kit includes a compound of the formulae described herein or a pharmaceutically acceptable salt, isomer, prodrug, or solvate thereof, and a label and/or instructions for use of the compounds in the treatment of the indications, including the diseases or conditions, described herein.

Provided herein are also articles of manufacture that include a compound of any of the formulae described herein or a pharmaceutically acceptable salt, isomer, prodrug, or solvate thereof, in a suitable container. The container may be a vial, jar, ampoule, preloaded syringe, and intravenous bag.

Pharmaceutical Compositions and Modes of Administration

Compounds provided herein are usually administered in the form of pharmaceutical compositions. Thus, provides herein are also pharmaceutical compositions that contain one or more of the compounds of any of the formulae disclosed herein or a pharmaceutically acceptable salt, isomers, prodrug, or solvate thereof, and one or more pharmaceutically acceptable vehicles selected from carriers, adjuvants and excipients. Suitable pharmaceutically acceptable vehicles may include, for example, inert solid diluents and fillers, diluents, including sterile aqueous solution and various organic solvents, permeation enhancers, solubilizers and adjuvants. Such compositions are prepared in a manner well known in the pharmaceutical art. See, e.g., Remington's Pharmaceutical Sciences, Mace Publishing Co., Philadelphia, Pa. 17th Ed. (1985); and Modern Pharmaceutics, Marcel Dekker, Inc. 3rd Ed. (G. S. Banker & C. T. Rhodes. Eds.).

The pharmaceutical compositions may be administered in either single or multiple doses. The pharmaceutical composition may be administered by various methods including, for example, rectal, buccal, intranasal, and transdermal routes. In certain embodiments, the pharmaceutical composition may be administered by intra-arterial injection, intravenously, intraperitoneally, parenterally, intramuscularly, subcutaneously, orally, topically, or as an inhalant. In some embodiments, the pharmaceutical composition is administered orally.

One mode for administration is parenteral, for example, by injection. The forms in which the pharmaceutical compositions described herein may be incorporated for administration by injection include, for example, aqueous or oil suspensions, or emulsions, with sesame oil, corn oil, cottonseed oil, or peanut oil, as well as elixirs, mannitol, dextrose, or a sterile aqueous solution, and similar pharmaceutical vehicles.

Oral administration may be another route for administration of the compounds described herein. Administration may be via, for example, capsule or enteric coated tablets. In making the pharmaceutical compositions that include at least one compound of any of the formulae described herein or a pharmaceutically acceptable salt, prodrug, or solvate thereof, the active ingredient is usually diluted by an excipient and/or enclosed within such a carrier that can be in the form of a capsule, sachet, paper or other container. When the excipient serves as a diluent, it can be in the form of a solid, semi-solid, or liquid material, which acts as a vehicle, carrier or medium for the active ingredient. Thus, the compositions can be in the form of tablets, pills, powders, lozenges, sachets, cachets, elixirs, suspensions, emulsions, solutions, syrups, aerosols (as a solid or in a liquid medium), ointments containing, for example, up to 10% by weight of the active compound, soft and hard gelatin capsules, sterile injectable solutions, and sterile packaged powders. In certain embodiments, the pharmaceutical composition is in the form of tablets.

Some examples of suitable excipients include lactose, dextrose, sucrose, sorbitol, mannitol, starches, gum *acacia*, calcium phosphate, alginates, tragacanth, gelatin, calcium silicate, microcrystalline cellulose, polyvinylpyrrolidone, cellulose, sterile water, syrup, and methyl cellulose. The formulations can additionally include lubricating agents such as talc, magnesium stearate, and mineral oil; wetting agents; emulsifying and suspending agents; preserving agents such as methyl and propylhydroxy-benzoates; sweetening agents; and flavoring agents.

The compositions that include at least one compound of any of the formulae described herein or a pharmaceutically acceptable salt, isomer, prodrug, or solvate thereof, can be formulated so as to provide quick, sustained or delayed release of the active ingredient after administration to the subject by employing procedures known in the art. Controlled release drug delivery systems for oral administration include osmotic pump systems and dissolutional systems containing polymer-coated reservoirs or drug-polymer matrix formulations. Examples of controlled release systems are given in U.S. Pat. Nos. 3,845,770; 4,326,525; 4,902,514; and 5,616,345. Another formulation for use in the methods of the present invention employs transdermal delivery devices ("patches"). Such transdermal patches may be used to provide continuous or discontinuous infusion of the compounds described herein in controlled amounts. The construction and use of transdermal patches for the delivery of pharmaceutical agents is well known in the art. See, e.g., U.S. Pat. Nos. 5,023,252, 4,992,445 and 5,001,139. Such patches may be constructed for continuous, pulsatile, or on demand delivery of pharmaceutical agents.

For preparing solid compositions such as tablets, the principal active ingredient may be mixed with a pharmaceutical excipient to form a solid preformulation composition containing a homogeneous mixture of a compound of any of the above formulae or a pharmaceutically acceptable salt, prodrug, or solvate thereof. When referring to these preformulation compositions as homogeneous, the active ingredient may be dispersed evenly throughout the composition so that the composition may be readily subdivided into equally effective unit dosage forms such as tablets, pills and capsules.

The tablets or pills of the compounds described herein may be coated or otherwise compounded to provide a dosage form affording the advantage of prolonged action, or to protect from the acid conditions of the stomach. For example, the tablet or pill can include an inner dosage and an outer dosage component, the latter being in the form of an envelope over the former. The two components can be separated by an enteric layer that serves to resist disintegration in the stomach and permit the inner component to pass intact into the duodenum or to be delayed in release. A variety of materials can be used for such enteric layers or coatings, such materials including a number of polymeric acids and mixtures of polymeric acids with such materials as shellac, cetyl alcohol, and cellulose acetate.

Compositions for inhalation or insufflation may include solutions and suspensions in pharmaceutically acceptable, aqueous or organic solvents, or mixtures thereof, and powders. The liquid or solid compositions may contain suitable pharmaceutically acceptable excipients as described supra. In some embodiments, the compositions are administered by the oral or nasal respiratory route for local or systemic effect. In other embodiments, compositions in pharmaceutically acceptable solvents may be nebulized by use of inert gases. Nebulized solutions may be inhaled directly from the nebulizing device or the nebulizing device may be attached to a facemask tent, or intermittent positive pressure breathing machine. Solution, suspension, or powder compositions may be administered, preferably orally or nasally, from devices that deliver the formulation in an appropriate manner.

Dosing

The specific dose level of a compound of the formulae described herein for any particular subject will depend upon a variety of factors including the activity of the specific compound employed, the age, body weight, general health, sex, diet, time of administration, route of administration, and rate of excretion, drug combination and the severity of the particular disease in the subject undergoing therapy. For example, a dosage may be expressed as a number of milligrams of a compound of the formula per kilogram of the subject's body weight (mg/kg). Dosages of between about 0.01 and 200 mg/kg may be appropriate. In some embodiments, about 0.01 and 150 mg/kg may be appropriate. In other embodiments a dosage of between 0.05 and 100 mg/kg may be appropriate. Normalizing according to the subject's body weight is particularly useful when adjusting dosages between subjects of widely disparate size, such as occurs when using the drug in both children and adult humans or when converting an effective dosage in a non-human subject such as dog to a dosage suitable for a human subject.

The daily dosage may also be described as a total amount of a compound of the formulae administered per dose or per day. Daily dosage of a compound may be between about 1 mg and 2,000 mg, between about 1,000 to 2,000 mg/day, between about 1 to 1,000 mg/day, between about 1 to 500 mg/day, between about 100 to 150 mg/day, between about 1 to 100 mg/day, between about between about 1 to 50 mg/day, between about 50 to 100 mg/day, between about 100 to 125 mg/day, between about 100 to 150 mg/day, between about 100 to 175 mg/day, between about 100 to 200 mg/day, between about 100 to 225 mg/day, between about 100 to 250 mg/day, between about 100 to 350 mg/day, between about 100 to 400 mg/day, between about 100 to 450 mg/day, or between about 100 to 500 mg/day.

When administered orally, the total daily dosage for a human subject may be between 1 mg and 1,000 mg/day, between about 1 to 100 mg/day, between about 1 to 50 mg/day, between about 50 to 100 mg/day, between 100 to 200 mg/day, between about 200 to 300 mg/day, between about 300 to 400 mg/day, between about 400 to 500 mg/day, between about 100 to 150 mg/day, between about 150 to 200 mg/day, between about 200 to 250 mg/day, between about 75 to 150 mg/day, or between about 150 to 300 mg/day.

The compounds of the present application or the compositions thereof may be administered once, twice, three, or four times daily, using any suitable mode described above. Also, administration or treatment with the compounds according to any of the formulae described herein may be continued for a number of days; for example, commonly treatment would continue for at least 7 days, 14 days, or 28 days, for one cycle of treatment. In some treatment, the compound or the composition thereof is administered continuously, i.e. every day. Treatment cycles are well known in cancer chemotherapy, and are frequently alternated with resting periods of about 1 to 28 days, commonly about 7 days or about 14 days, between cycles. The treatment cycles, in other embodiments, may also be continuous.

In a particular embodiment, the method comprises administering to the subject an initial daily dose of about 1 to 500 mg of a compound of the above formula and increasing the dose by increments until clinical efficacy is achieved. Increments of about 1, 5, 10, 25, 50, 75, or 100) mg can be used to increase the dose. The dosage can be increased daily, every other day, twice per week, or once per week.

Synthesis of the Compounds

The compounds of the present application may be prepared using the methods disclosed herein and routine modifications thereof, which will be apparent given the disclosure herein and methods well known in the art. Conventional and well-known synthetic methods may be used in addition to the teachings herein. The synthesis of typical compounds described herein may be accomplished as described in the following examples. If available, reagents may be purchased commercially, e.g., from Sigma Aldrich or other chemical suppliers. In general, compounds described herein are typically stable and isolatable at room temperature and pressure.

General Synthesis

Typical embodiments of compounds described herein may be synthesized using the general reaction schemes described below. It will be apparent given the description herein that the general schemes may be altered by substitution of the starting materials with other materials having similar structures to result in products that are correspondingly different. Descriptions of syntheses follow to provide numerous examples of how the starting materials may vary to provide corresponding products. Given a desired product for which the substituent groups are defined, the necessary starting materials generally may be determined by inspection. Starting materials are typically obtained from commercial sources or synthesized using published methods. For synthesizing compounds which are embodiments described in the present disclosure, inspection of the structure of the compound to be synthesized will provide the identity of each substituent group. The identity of the final product will generally render apparent the identity of the necessary starting materials by a simple process of inspection, given the examples herein.

Synthetic Reaction Parameters

The terms "solvent", "inert organic solvent", or "inert solvent" refer to a solvent inert under the conditions of the reaction being described in conjunction therewith (including, for example, benzene, toluene, acetonitrile, tetrahydrofuran ("THF"), dimethylformamide ("DMF"), chloroform, methylene chloride (or dichloromethane), diethyl ether, methanol, and the like). Unless specified to the contrary, the solvents used in the reactions of the present invention are inert organic solvents, and the reactions are carried out under an inert gas, preferably nitrogen.

The compounds of formula (J) may be prepared using the method shown in Reaction Scheme I. The compounds of formula (I) may be prepared using the method shown in Reaction Scheme I, wherein R4 is optionally substituted pyrimidine.

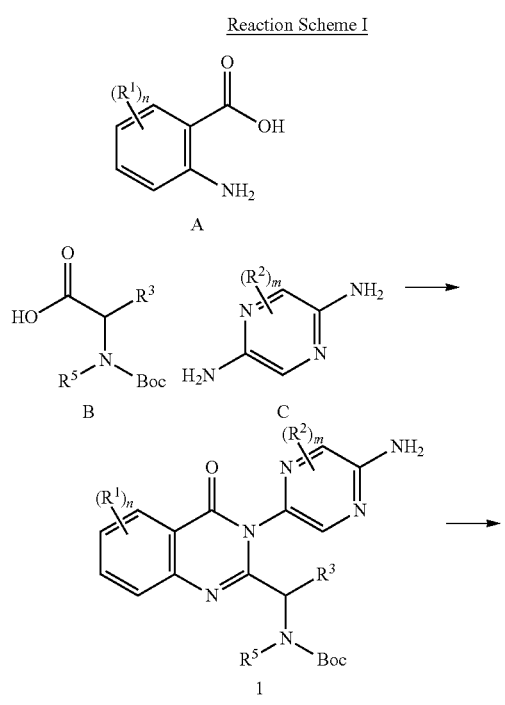

Reaction Scheme I

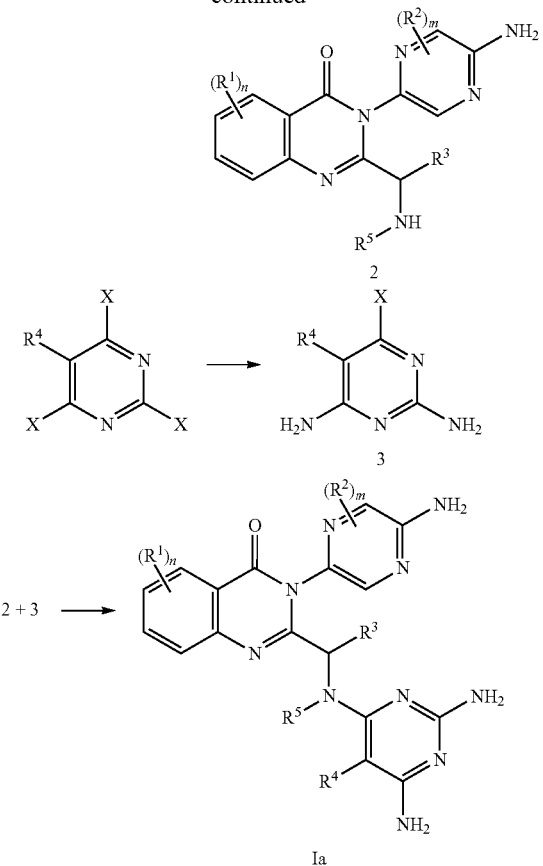

Step 1—Preparation of a Compound of Formula (1)

The compound of formula (1) can be made by combining compounds (A), (B) and (C) in the presence of a dehydrating agent. Compounds (A), (B) and (C) are commercially available or can be made by methods known in the art. With respect to compound (A), $R^1$ is as defined herein. With respect to compound (B), $R^3$ and $R^5$ is as defined herein. With respect to compound (C), $R^2$ is as defined herein. Compound (A) can be mixed with Compound (B) in the presence of a coupling agent such as diphenyl phosphite in a solvent such as pyridine. After stirring at a temperature between ambient and 100° C. for between 1 and 5 hours, compound (C) is added. After further stirring at a temperature between ambient and 100° C. for between 5 and 24 hours, the reaction mixture is allowed to cool to room temperature. To extract the compound of formula (1), an organic solvent such as ethyl acetate (EtOAc) may be added, followed by washing with, mild acid, water, and brine. The organic phase can be concentrated to obtain the compound of formula (1). Alternatively, the residue may be purified directly without an aqueous work-up. The compound of formula (1) may be purified by any suitable methods known in the art, such as chromatography on silica gel. Alternatively, the compound of formula (1) may be used in the next step without purification.

Step 2—Preparation of a Compound of Formula (2)

The compound of formula (2) can be made by removing the protecting group(s) from the compound of formula (1). The compound of formula (1) is dissolved in a suitable solvent and treated with a suitable acid. Suitable solvents may include, for example, dichloromethane, dioxane, or other suitable solvents. Suitable acids may include, for example, trifluoroacetic acid, hydrochloric acid, or boron tribromide ($BBr_3$). The reaction can be carried out at temperatures between −78° C. to ambient temperature. On reaction completion, solvent is removed to obtain the compound of formula (2). In the case of a reaction using $BBr_3$ the reaction may first be treated with MeOH before an aqueous work-up to obtain a compound of formula (2).

Step 4—Preparation of a Compound of Formula (3)

The compound of formula (3) can be made by treating 5-substituted-2,4,6-trihalopyrimidine with ammonium hydroxide in a suitable solvent such as dioxane, where the halo is either chloro or fluoro. The reaction is carried out at an elevated temperature between 30 and 80° C. for a suitable time, typically between 2 and 8 hours or when the reaction is complete. Upon completion, water is added to the cooled solution, and the precipitate is collected by filtration. The nitrile can be converted to the carboxamide under standard conditions.

Step 5—Preparation of a Compound of Formula (I)

The compound of formula (Ia) can generally be prepared by coupling compound of formula (3) and compound of formula (2) in the presence of a suitable base in a suitable solvent. An example of a suitable base is diisopropylethylamine. An example of a suitable solvent is N-methylpyrrolidone (NMP). The reaction is typically performed at a temperature between 50° C. to 150° C. for about 30 minutes to 24 hours. Alternatively the reaction can be performed in a microwave at a temperature between 100° C. to 150° C. for about 30 minutes to 24 hours. Water can be added to quench the reaction upon completion, and the precipitate may be filtered and then dissolved in an organic solvent such as dichloromethane (DCM). The product can be isolated by methods known in the art, for example by removal of solvent under reduced pressure. The product can be purified using any suitable methods known in the art, for example, chromatography of the residue on a silica column. Furthermore, compounds of formula (I) may be prepared by coupling compounds of formula (2) with appropriately substituted heterocycles of the general formula $R^4$—X in a similar manner.

After synthesis, the compounds may be isolated in the form of a free base or a salt (which includes and is not limited to a hydrochloric acid salt form or a trifluoroacetic acid salt form) and characterized by NMR. Thus, the resulting compounds and their NMR characterizations may be either the free base or salt. The ratio of parent and corresponding salt is not determined.

EXAMPLE 1

Preparation of a Compound of Formula (1)

A. Preparation of a Compound of Formula (1) in which n is 2, $R^1$ is Chloro and Fluoro, m is 0, $R^5$ is H, and $R^3$ is Methyl

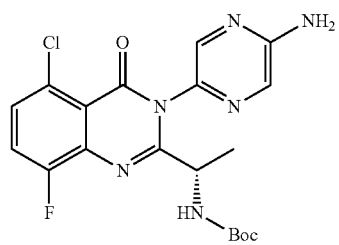 [SMILES: C[C@H](NC(=O)OC(C)(C)C)c1nc2c(F)ccc(Cl)c2c(=O)n1-c1cnc(N)cn1]

A mixture of 2-amino-6-chloro-3-fluorobenzoic acid (1.43 g, 7.6 mmol) and Boc-L-alanine (1.7 g, 9.1 mmol) in pyridine (4.9 mL, 60.5 mmol) was warmed to 45° C. until homogeneous then allowed to cool to room temperature, at which time diphenyl phosphite (5.0 mL, 26 mmol) was added. The mixture was stirred for one hour at 45° C., then treated with pyrazine-2,5-diamine bis HCl (1 g, 9.1 mmol) in a single portion. The mixture was stirred overnight at 55° C. After cooling to room temperature, the mixture was diluted with toluene (20 mL) and washed three times with 10% aqueous hydrochloric acid solution, and concentrated to dryness under reduced pressure. The residue was chromatographed, using a 25 g SiliaSep flash column, eluting with hexanes to 65% ethyl acetate. The combined fractions were concentrated under reduced pressure to give (S)-tert-butyl (1-(3-(5-amninopyrazin-2-yl)-5-chloro-8-fluoro-4-oxo-3,4-dihydroquinazolin-2-yl)ethyl)carbamate. ES/MS 435.1 (M+H$^+$).

B. Preparation of the Below Compounds of Formula (1) Using the Procedures Described in Example 1A and Reaction Scheme I (S)-tert-butyl (1-(3-(5-aminopyrazin-2-yl)-8-fluoro-4-oxo-3,4-dihydroquinazolin-2-yl)ethyl)carbamate;

(S)-tert-butyl (1-(3-(5-aminopyrazin-2-yl)-5-chloro-4-oxo-3,4-dihydroquinazolin-2-yl)ethyl)carbamate;

(S)-tert-butyl ((3-(5-aminopyrazin-2-yl)-5-chloro-4-oxo-3,4-dihydroquinazolin-2-yl)(cyclopropyl)methyl)carbamate;

(S)-tert-butyl (1-(3-(5-aminopyrazin-2-yl)-6,8-difluoro-4-oxo-3,4-dihydroquinazolin-2-yl)ethyl)carbamate;

(S)-tert-butyl (1-(3-(5-aminopyrazin-2-yl)-8-chloro-6-fluoro-4-oxo-3,4-dihydroquinazolin-2-yl)ethyl)carbamate;

(S)-tert-butyl ((3-(5-aminopyrazin-2-yl)-5,8-dichloro-4-oxo-3,4-dihydroquinazolin-2-yl)(cyclopropyl)methyl)carbamate; and (S)-tert-butyl (1-(3-(5-aminopyrazin-2-yl)-5,8-dichloro-4-oxo-3,4-dihydroquinazolin-2-yl)ethyl)carbamate.

EXAMPLE 2

Preparation of a Compound of Formula (2)

A. Preparation of a Compound of Formula (2) in which n is 2, $R^1$ is Chloro and Fluoro, m is 0, $R^5$ is H, and $R^3$ is Methyl

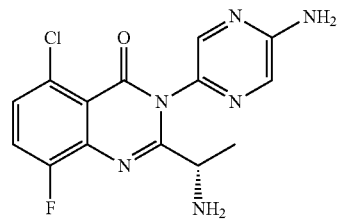 [SMILES: C[C@H](N)c1nc2c(F)ccc(Cl)c2c(=O)n1-c1cnc(N)cn1]

A solution of (give (S)-tert-butyl (1-(3-(5-aminopyrazin-2-yl)-5-chloro-8-fluoro-4-oxo-3,4-dihydroquinazolin-2-yl)ethyl)carbamate (0.4 g, 0.92 mmol) in dichloromethane (10 mL) was treated with trifluoroacetic acid (0.7 mL). After stirring 2 h at room temperature, the mixture was concentrated to dryness under reduced pressure to give (S)-2-(1-aminoethyl)-3-(5-aminopyrazin-2-yl)-5-chloro-8-fluoroquinazolin-4(3H)-one as a golden amorphous semi-solid, which was carried forward without further purification. ES/MS 335.1 (M+H$^+$).

B. Preparation of the Below Compounds of Formula (2) Using the Procedure Described in Example 2A and Reaction Scheme 1
(S)-2-(1-aminoethyl)-3-(5-aminopyrazin-2-yl)-8-fluoroquinazolin-4(3H)-one;
(S)-2-(1-aminoethyl)-3-(5-aminopyrazin-2-yl)-5-chloroquinazolin-4(3H)-one;
(S)-2-(amino(cyclopropyl)methyl)-3-(5-aminopyrazin-2-yl)-5-chloroquinazolin-4(3H)-one;
(S)-2-(1-aminoethyl)-3-(5-aminopyrazin-2-yl)-6,8-di fluoroquinazolin-4(3H)-one;
(S)-2-(1-aminoethyl)-3-(5-aminopyrazin-2-yl)-8-chloro-6-fluoroquinazolin-4(3H)-one;
(S)-2-(amino(cyclopropyl)methyl)-3-(5-aminopyrazin-2-yl)-5,8-dichloroquinazolin-4(3H)-one; and
(S)-2-(1-aminoethyl)-3-(5-aminopyrazin-2-yl)-5,8-dichloroquinazolin-4(3H)-one.

EXAMPLE 3

Preparation of a Compound of Formula (3)

A. Preparation of a compound of formula (3) in which $R^4$ is CN and X is Cl (2,4-diamino-6-chloropyrimidine-5-carbonitrile)

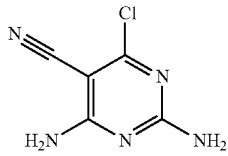 [SMILES: N#Cc1c(N)nc(N)nc1Cl]

Ammonium hydroxide (20 mL) was added to a solution of 2,4,6-trichloropyrimidine-5-carbonitrile (5.0 g, 24 mmol) in dioxane (20 mL) at room temperature. The solution was warmed to 50° C. and stirred for 3 hrs. The reaction mixture was cooled to 10° C. and water (50 mL) was added. The resulting solid was filtered, washed with water, and dried under high vacuum to afford the title compound as a white solid. $^{13}$H NMR (100 MHz, DMSO) 164.8, 162.6, 161.9, 115.8, 77.6. ES/MS m/z=169.9 (M+H)$^+$.

B. Preparation of the Below Compounds of Formula (3) Using the Procedures Described in Example 3A and Reaction Scheme 1
5-chloro-6-fluoropyrimidine-2,4-diamine;
6-chloro-5-(methylsulfonyl)pyrimidine-2,4-diamine
6-chloro-5-(trifluoromethyl)pyrimidine-2,4-diamine; and
2,4-diamino-6-chloropyrimidine-5-carboxamide.

EXAMPLE 4

Preparation of a Compound of Formula (I)

A. Preparation of a Compound of Formula (1) in which n is 2, $R^1$ is Chloro and Fluoro, m is 0, $R^5$ is H, and $R^3$ is methyl, which is (S)-3-(5-aminopyrazin-2-yl)-5-chlor-2-(1-((2,6-diamino-5-chloropyrimidin-4-yl)amino)ethyl)-8-fluoroquinazolin-4(3H)-one (Compound 1)

5-chloro-6-fluoropyrimidine-2,4-diamine (0.11 g, 0.69 mmol) and DIEA (0.4 mL, 2.3 mmol) were added to a solution of (S)-2-(l-aminoethyl)-3-(5-aminopyrazin-2-yl)-5-chloro-8-fluoroquinazolin-4(3H)-one (0.15 g, 0.46 mmol) in IPA. The resulting mixture was heated to 120° C. for 4 h in a microwave then concentrated. HPLC purification of the residue afforded the title compound. $^1$H NMR (400 MHz, DMSO-d$_6$) δ 8.01 (s, 1H), 7.85-7.71 (m, 3H), 7.63 (dd, J=8.7, 4.5 Hz, 1H), 7.54 (s, 2H), 7.43 (s, 3H), 6.86 (s, 2H), 5.01-4.91 (m, 1H), 1.43 (d, J=6.5 Hz, 3H). ES/MS 477.1 (M+H$^+$).

B. Preparation of the Below Compound of Formula (I), Using the Procedures Described Example 4A and Reaction Scheme I
(S)-2,4-diamino-6-((1-(3-(5-aminopyrazin-2-yl)-5-chloro-8-fluoro-4-oxo-3,4-dihydroquinazolin-2-yl)ethyl)amino) pyrimidine-5-carbonitrile (Compound 2). $^1$H NMR (400 MHz, DMSO-d$_6$) δ 8.20-7.92 (m, 4H), 7.92-7.73 (m, 3H), 7.71-7.56 (m, 2H), 7.49-7.35 (m, 1H), 6.87 (s, 2H), 5.01 (q, J=6.8 Hz, 1H), 1.42 (d, J=6.7 Hz, 3H). ES/MS 468.1 (M+H)$^+$;

(S)-4-amino-6-((1-(3-(5-aminopyrazin-2-yl)-5-chloro-8-fluoro-4-oxo-3,4-dihydroquinazolin-2-yl)ethyl)amino) pyrimidine-5-carbonitrile (Compound 3). $^1$H NMR (400 MHz, DMSO-d$_6$) δ 8.54 (s, 1H), 8.09-8.02 (m, 2H), 7.94 (s, 1H), 7.84-7.71 (m, 2H), 7.60 (dd, J=8.8, 4.3 Hz, 1H), 7.44 (s, 2H), 6.86 (s, 2H), 4.85-4.80 (m, 1H), 1.42 (d, J=7.4 Hz, 3H). ES/MS 453.1 (M+H)$^+$;

(S)-2-(1-((3H-[1,2,3]triazolo[4,5-d]pyrimidin-7-yl)amino) ethyl)-3-(5-aminopyrazin-2-yl)-8-fluoroquinazolin-4 (3H)-one (Compound 4). $^1$H NMR (400 MHz, DMSO-d$_6$) δ 9.51 (s, 1H), 8.41 (m, 3H), 7.93 (t, J=9.1 Hz, 1H), 7.74-7.64 (m, 1H), 7.53 (td, J=8.3, 4.7 Hz, 1H), 7.46-7.17 (in, 4H), 4.86-4.68 (m, 1H), 1.66 (d, J=6.8 Hz, 3H). ES/MS 420.1 (M+H)$^+$;

(S)-3-(5-amninopyrazin-2-yl)-5-chloro-8-fluoro-2-(1-(furo [2,3-d]pyrimidin-4-ylamino)ethyl)quinazolin-4(3H)-one (Compound 5). $^1$H NMR (400 MHz, DMSO-d$_6$) δ 8.51 (s, 1H), 8.17-8.10 (m, 2H), 8.03 (s, 1H), 7.91-7.67 (m, 3H), 7.58 (m, 1H), 7.25 (m, 2H), 7.08 (s, 1H), 4.78 (m, 1H), 1.52 (d, J=6.8 Hz, 3H). ES/MS 453.1 (M+H$^+$);

(S)-2,4-diamino-6-((1-(3-(5-aminopyrazin-2-yl)-5-chloro-4-oxo-3,4-dihydroquinazolin-2-yl)ethyl)amino)pyrimidine-5-carbonitrile (Compound 6). 1H NMR (400 MHz, DMSO-d6) δ 8.18 (s, 1H), 8.03 (s, 3H), 7.82 (t, J=8.0 Hz, 2H), 7.65 (ddd, J=20.3, 8.0, 1.2 Hz, 2H), 7.49 (brs, 1H), 7.02-6.71 (brs, 3H), 4.99 (q, J=6.8 Hz, 1H), 1.45-1.38 (m, 3H). ES/MS 450.1 (M+H)$^+$:

(S)-3-(5-aminopyrazin-2-yl)-5-chloro-2-(1-((2,6-diamino-5-chloropyrimidin-4-yl)amino)ethyl)quinazolin-4(3H)-one (Compound 7). 1H NMR (400 MHz, DMSO-d6) δ 8.02 (brs, 1H), 7.86-7.77 (m, 3H), 7.69 (dd, J=8.1, 1.2 Hz, 1H), 7.62 (dd, J=7.9, 1.2 Hz, 1H), 7.55 (brs, 2H), 7.44 (brs, 2H), 6.84 (brs, 2H), 4.94 (p, J=6.8 Hz, 1H), 1.42 (d, J=6.6 Hz, 3H). ES/MS 459.1 (M+H$^+$):

(S)-3-(5-aminopyrazin-2-yl)-5-chloro-2-(cyclopropyl((2,6-diamino-5-chloropyrimidin-4-yl)amino)methyl)quinazolin-4(3H)-one (Compound 8). 1H NMR (400 MHz, DMSO-d6) δ 7.88-7.78 (m, 2H), 7.78-7.66 (m, 3H), 7.63 (dd, J=7.8, 1.2 Hz, 1H), 7.56 (s, 2H), 7.41 (s, 2H), 6.82-6.73 (m, 2H), 4.74-4.47 (m, 1H), 1.53 (s, 1H), 0.57 (s, 1H), 0.46 (dp, J=12.4, 7.3, 6.1 Hz, 2H), 0.16 (dq, J=9.6, 4.9 Hz, 1H). ES/MS 485.1 (M+H)$^+$;

(S)-2,4-diamino-6-(((3-(5-aminopyrazin-2-yl)-5-chloro-4-oxo-3,4-dihydroquinazolin-2-yl(cyclopropyl)methyl) amino)pyrimidine-5-carbonitrile (Compound 9). 1H NMR (400 MHz, DMSO-d6) δ 8.14 (d, J=19.0 Hz, 3H), 7.90-7.78 (m, 2H), 7.71 (dd, J=8.2, 1.2 Hz, 1H), 7.63 (dd, J=7.8, 1.2 Hz, 1H), 7.48 (brs, 1H), 6.75 (m, 2H), 5.96 (brs, 2H), 4.69 (t, J=8.3 Hz, 1H), 1.54 (s, 1H), 0.57 (s, 1H), 0.51-0.39 (m, 2H), 0.17 (m, 1H). ES/MS 476.1 (M+H)$^+$;

(S)-2,4-diamino-6-(((3-(5-aminopyrazin-2-yl)-5,8-dichloro-4-oxo-3,4-dihydroquinazolin-2-yl)(cyclopropyl)methyl) amino)pyrimidine-5-carbonitrile (Compound 10). 1H NMR (400 MHz, DMSO-d6) δ 8.07-7.97 (m, 5H), 7.91-7.82 (m, 1H), 7.80 (s, 1H), 7.63 (d, J=8.5 Hz, 1H), 7.47-7.41 (m, 2H), 6.85 (s, 2H), 4.82 (t, J=7.9 Hz, 1H), 0.57-0.39 (m, 4H), 0.24-0.13 (m, 1H). ES/MS 510.1 (M+H$^+$);

(S)-2,4-diamino-6-((1-(3-(5-aminopyrazin-2-yl)-5,8-dichloro-4-oxo-3,4-dihydroquinazolin-2-yl)ethyl)amino)pyrimidine-5-carbonitrile (Compound 11). 1H NMR (400 MHz, DMSO-d6) δ 8.11-7.90 (m, 5H), 7.83 (s, 2H), 7.62 (d, J=8.5 Hz, 1H), 7.54-7.26 (m, 2H), 6.90 (s, 2H), 5.07 (p, J=6.7 Hz, 1H), 1.43 (d, J=6.6 Hz, 3H). ES/MS 484.1 (M+H$^+$)$^+$;

(S)-3-(5-aminopyrazin-2-yl)-5,8-dichloro-2-(cyclopropyl((2,6-diamino-5-chloropyrimidin-4-yl)amino)methyl)quinazolin-4(3H)-one (Compound 12). 1H NMR (400 MHz, DMSO-d6) δ 8.52 (d, J=1.5 Hz, 1H), 8.07-8.00 (m, 2H), 7.70 (d, J=1.5 Hz, 1H), 7.63 (d, J=8.6 Hz, 1H), 7.49 (d, J=8.5 Hz, 1H), 6.89-6.81 (m, 3H), 6.45 (s, 2H), 6.15 (d, J=5.3 Hz, 1H), 4.81-4.76 (m, 1H), 1.38-1.12 (m, 1H), 1.06-0.72 (m, 2H), 0.66-0.39 (m, 2H). ES/MS 519.1 (M+H$^+$);

(S)-3-(5-aminopyrazin-2-yl)-5,8-dichloro-2-(1-((2,6-diamino-5-chloropyrimidin-4-yl)amino)ethyl)quinazolin-4(3H)-one (Compound 13). 1H NMR (400 MHz, DMSO-d6) δ 8.02 (dd, J=8.6, 0.7 Hz, 2H), 7.84 (d, J=8.1 Hz, 2H), 7.67-7.56 (m, 3H), 7.56-7.46 (m, 2H), 6.95-6.87 (m, 3H), 5.01 (p, J=6.7 Hz, 1H), 1.44 (d, J=6.6 Hz, 3H). ES/MS 493.0 (M+H$^+$);

(S)-2-amino-4-((1-(3-(5-aminopyrazin-2-yl)-8-chloro-6-fluoro-4-oxo-3,4-dihydroquinazolin-2-yl)ethyl)amino)-6-(difluoromethyl)pyrimidine-5-carbonitrile (Compound 14). $^1$H NMR (400 MHz, DMSO) δ 8.16 (dd, J=8.5, 2.9 Hz, 1H), 8.08 (br s, 1H), 7.86-7.79 (m, 3H), 7.54 (br s, 1H), 7.35 (br s, 1H), 6.87 (br s, 2H), 6.65 (t, J=53.5 Hz, 1H), 5.10-5.00 (m, 1H), 1.45 (d, J=6.5 Hz, 3H). ES/MS 503.1 (M+H$^+$);

(S)-2,4-Diamino-6-((1-(3-(5-aminopyrazin-2-yl)-6,8-difluoro-4-oxo-3,4-dihydroquinazolin-2-yl)ethyl)amino)pyrimidine-5-carbonitrile (Compound 15). $^1$H NMR (400 MHz, DMSO-d$_6$) δ 8.00 (s, 3H), 7.92 (ddd, J=10.3, 8.9, 2.9 Hz, 1H), 7.79 (s, 1H), 7.69 (ddd, J=8.2, 2.9, 1.3 Hz, 1H), 6.85 (s, 2H), 5.01 (p, J=6.7 Hz, 1H), 1.40 (d, J=6.6 Hz, 3H). ES/MS 468.1 (M+H$^+$);

(S)-3-(5-Aminopyrazin-2-yl)-2-(1-((2,6-diamino-5-chloropyrimidin-4-yl)amino)ethyl)-6,8-difluoroquinazolin-4(3H)-one (Compound 16). $^1$H NMR (400 MHz, DMSO-d$_6$) δ 7.93 (ddd. J=10.4, 8.9, 2.9 Hz, 2H), 7.79 (d, J=7.8 Hz, 2H), 7.69 (ddd, J=8.2, 2.9, 1.3 Hz, 1H), 7.50 (s, 2H), 7.39 (s, 3H), 6.84 (s, 2H), 4.99 (p, J=6.7 Hz, 1H), 1.41 (d, J=6.6 Hz, 3H). ES/MS 461.9 (M+H$^+$);

(S)-2,4-Diamino-6-((1-(3-5-aminopyrazin-2-yl)-8-chloro-6-fluoro-4-oxo-3,4-dihydroquinazolin-2-yl)ethyl)amino)pyrimidine-5-carbonitrile (Compound 17). $^1$H NMR (400 MHz, DMSO-d$_6$) δ 8.17 (dd, J=8.5, 2.9 Hz, 1H), 8.02 (s, 2H), 7.85 (tt, J=7.8, 3.6 Hz, 4H), 6.90 (s, 2H), 5.10 (p, J=6.6 Hz, 1H), 1.44 (d, J=6.6 Hz, 3H). ES/MS 468.1 (M+H$^+$);

(S)-3-(5-Aminopyrazin-2-yl)-8-chloro-2-(1-((2,6-diamino-5-chloropyrimidin-4-yl)amino)ethyl)-6-fluoroquinazolin-4(3H)-one (Compound 18). $^1$H NMR (400 MHz, DMSO-d$_6$) δ 8.19 (dd, J=8.5, 2.9 Hz, 1H), 7.98 (s, 2H), 7.86 (dd, J=8.1, 2.9 Hz, 21H), 7.81 (s, 1H), 7.56 (s, 4H), 6.90 (s, 2H), 5.23-4.91 (m, 1H), 1.45 (d, J=6.6 Hz, 3H). ES/MS 477.1 (M+H$^+$);

(S)-2-(1-((6-Amino-5-chloropyrimidin-4-yl)amino)ethyl)-3-(5-aminopyrazin-2-yl)-5-chloroquinazolin-4(3H)-one (Compound 19). $^1$H NMR (400 MHz, DMSO-d$_6$) δ 8.73 (s, 1H), 8.18 (d, J=1.4 Hz, 1H), 7.92 (s, 1H), 7.89 (d, J=1.5 Hz, 1H), 7.67-7.60 (m, 1H), 7.49 (dd, J=8.2, 1.2 Hz, 1H), 7.44 (dd, J=7.8, 1.2 Hz, 1H), 7.18 (s, 2H), 4.75 (s, 1H), 1.49 (d, J=7.0 Hz, 3H). ES/MS 444.1 (M+H$^+$);

(S)-2-(((6-Amino-5-chloropyrimidin-4-yl)amino)(cyclopropyl)methyl)-3-(5-aminopyrazin-2-yl)-5,8-dichloroquinazolin-4(3H)-one (Compound 20). $^1$H NMR (400 MHz, DMSO-d$_6$) δ 8.01 (d, J=8.5 Hz, 1H), 7.82 (s, 1H), 7.71 (s, 1H), 7.60 (d, J=8.5 Hz, 1H), 6.87 (s, 2H), 6.62 (d, J=17.2 Hz, 3H), 4.67 (s, 1H), 1.42 (s, 1H), 0.51-0.27 (m, 4H), 0.27-0.07 (m, 1H). ES/MS 504.1 (M+H$^+$); and (S)-2-(((6-Amino-5-chloropyrimidin-4-yl)amino)(cyclopropyl)methyl)-3-(5-aminopyrazin-2-yl)-5-chloroquinazolin-4(3H)-one (Compound 21). $^1$H NMR (400 MHz, DMSO-d$_6$) δ 7.96 (s, 1H), 7.81 (q, J=7.9 Hz, 2H), 7.69 (d, J=9.3 Hz, 3H), 7.60 (dd, J=7.9, 1.3 Hz, 2H), 6.81 (s, 3H), 6.61 (s, 4H), 4.37 (d, J=12.5 Hz, 1H), 1.49 (d, J=12.0 Hz, 1H), 0.44 (s, 4H), 0.34 (q, J=4.5 Hz, 1H). ES/MS 470.1 (M+H).

Biological Examples

The compounds of formula (I) were characterized for their enzymatic activity against the PI3K isoforms. The activities were measured using a time-resolved fluorescence resonance energy transfer (TR-FRET) assay. TR-FRET monitored the formation of 3,4,5-inositol triphosphate molecule that competed with fluorescently labeled PIP3 for binding to the GRP-1 pleckstrin homology domain protein. An increase in phosphatidylinositide 3-phosphate product resulted in a decrease in TR-FRET signal as the labeled fluorophore was displaced from the GRP-1 protein binding site.

Class I PI3K isoforms were expressed and purified as heterodimeric recombinant proteins. All assay reagents and buffers for the TR-FRET assay were purchased from Millipore. PI3K isoforms were assayed under initial rate conditions in the presence of 25 mM Hepes (pH 7.4), and 2×Km ATP (75-500 μM), 2 μM PIP2, 5% glycerol, 5 mM MgCl$_2$, 50 mM NaCl, 0.05% (v/v) Chaps, 1 mM dithiothreitol, and 1% (v/v) DMSO at the following concentrations for each isoform: PI3Kα, PI3Kβ, and PI3Kδ between 25 and 50 μM, and PI3Kγ at 2 nM. The compounds of Table 1 and Compound X ((S)-2,4-diamino-6-((1-(5-chloro-4-oxo-3-(pyridin-3-yl)-3,4-dihydroquinazolin-2-yl)ethyl)amino)pyrimidine-5-carbonitrile) and Compound Y ((S)-2,4-diamino-6-((1-(5-chloro-4-oxo-3-(pyridin-3-yl)-3,4-dihydroquinazolin-2-yl)ethyl)amino)pyrimidine-5-carbonitrile) were added to the assay solution and incubated for 30 minutes at 25° C. The reactions were terminated with a final concentration of 10 mM EDTA, 10 nM labeled-PIP3, and 35 nM Europium labeled GRP-1 detector protein before reading TR-FRET on an Envision plate reader (Ex: 340 nm; Em: 615/665 nm; 100 μs delay and 500 μs read window).

The results were normalized based on positive (1 μM wortmanin) and negative (DMSO) controls, and the IC$_{50}$ values for PI3K α, β, δ and γ were calculated from the fit of the dose-response curves to a four-parameter equation. These assays generally produced results within 3-fold of the reported mean.

Table 2 summarizes the IC$_{50}$ (nM) values for PI3K isoforms β, δ, and γ. The results indicate that certain compounds of formula (1) inhibit both PI3Kδ and PI3Kβ. Also, Compound X exhibited PI3Kδ IC$_{50}$ of 0.2 nM, PI3Kβ IC$_{50}$ of 11 nM. PI3Kγ IC$_{50}$ of 7 nM. The PI3Kγ/PI3Kβ ratio for Compound X is 0.6. The results indicate that certain compounds have greater selectivity for PI3Kβ over PI3Kγ compared to compound X. Compounds in Table 1a were analyzed using the same assay, and the results are summarized in Table 2a.

TABLE 2

The $IC_{50}$ values (nM) for PI3K isoforms β, δ, and γ.

| Compound | PI3Kβ | PI3Kδ | PI3Kγ |
|---|---|---|---|
| 1 | 54 | 26 | >10000 |
| 2 | 4.4 | 3.5 | 630 |
| 3 | 74 | 11 | >10000 |
| 4 | >10000 | 2700 | >10000 |
| 5 | 5800 | 2300 | >10000 |
| 6 | 2.0 | 2.0 | 280 |
| 7 | 47 | 24 | 4000 |
| 8 | 190 | 24 | >10000 |
| 9 | 4.2 | 2.7 | 900 |
| 10 | 3.6 | 2.4 | 3100 |
| 11 | 1.8 | 1.9 | 1500 |
| 12 | 1200 | 97 | >10000 |
| 13 | 170 | 31 | >10000 |

TABLE 2a

The $IC_{50}$ values (nM) for PI3K isoforms β, δ, and γ.

| Compound | PI3Kβ | PI3Kδ | PI3Kγ |
|---|---|---|---|
| 14 | 200 | 340 | >10000 |
| 15 | 9.8 | 53 | 1500 |
| 16 | 530 | 780 | >10000 |
| 17 | 14 | 32 | 4900 |
| 18 | 570 | 500 | >10000 |
| 19 | 360 | 54 | >10000 |
| 20 | 1100 | 26 | >10000 |
| 21 | 720 | 30 | >10000 |

All of the U.S. patents, U.S. patent application publications, U.S. patent applications, foreign patents, foreign patent applications and non-patent publications referred to in this specification are incorporated herein by reference, in their entirety to the extent not inconsistent with the present description. From the foregoing it will be appreciated that, although specific embodiments of the invention have been described herein for purposes of illustration, various modifications may be made without deviating from the spirit and scope of the present application.

What is claimed:
1. A compound having the structure of formula (I):

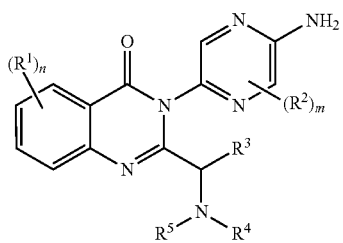

wherein:
n is 1, 2, or 3;
m is 0 or 1;
each $R^1$ is independently selected from halo, cyano, optionally substituted $C_{1-6}$ alkyl, $C_{1-6}$ haloalkyl, $C_{1-6}$ alkoxy, optionally substituted sulfonyl, optionally substituted $C_{6-10}$ aryl, $C_{3-8}$ heteroaryl, optionally substituted $C_{3-8}$ cycloalkyl, and $C_{2-8}$ heterocycloalkyl; wherein the optionally substituted $C_{1-6}$ alkyl is a $C_{1-6}$ alkyl group optionally substituted with one, two, or three members of hydroxyl, halo, $C_{1-6}$ alkoxy, $C_{3-8}$ cycloalkyl, $C_{2-8}$ heterocycloalkyl, $C_{6-10}$ or $C_{3-8}$ heteroaryl; wherein the optionally substituted sulfonyl is a sulfonyl group optionally substituted with $C_{1-6}$ alkyl, $C_{3-8}$ cycloalkyl, $C_{2-8}$ heterocyclyl, $C_{6-10}$ aryl, or $C_{3-8}$ heteroaryl; wherein the optionally substituted $C_{6-10}$ aryl is an $C_{6-10}$ aryl group optionally substituted with one, two, or three members of halo, $C_{1-6}$ alkyl, $C_{1-6}$ haloalkyl, $C_{2-8}$ heterocycloalkyl $C_{3-8}$ heteroaryl, $C_{1-6}$ alkoxy, or cyano; wherein the optionally substituted $C_{3-8}$ cycloalkyl is a $C_{3-8}$ cycloalkyl group optionally substituted with one, two, or three members of $C_{1-6}$ alkyl, $C_{1-6}$ haloalkyl, $C_{2-8}$ heterocycloalkyl, $C_{6-10}$ aryl, $C_{3-8}$ heteroaryl, $C_{1-6}$ alkoxy, halo, or hydroxyl;
each $R^2$ is independently selected from halo and optionally substituted $C_{1-6}$ alkyl; wherein the optionally substituted $C_{1-6}$ alkyl is a $C_{1-6}$ alkyl group optionally substituted with one, two, or three members of hydroxyl, halo, $C_{1-6}$ alkoxy, $C_{3-8}$ cycloalkyl, $C_{2-8}$ heterocycloalkyl, $C_{6-10}$ aryl, or $C_{3-8}$ heteroaryl,
$R^3$ is hydrogen, optionally substituted $C_{1-6}$ alkyl, optionally substituted $C_{6-10}$ aryl, or optionally substituted $C_{3-8}$ cycloalkyl; wherein the optionally substituted $C_{1-6}$ alkyl is a $C_{1-6}$ alkyl group optionally substituted with one, two, or three members of hydroxyl, halo $C_{1-6}$ alkoxy, $C_{3-8}$ cycloalkyl, $C_{2-8}$ heterocycloalkyl, $C_{6-10}$ aryl, or $C_{3-8}$ heteroaryl; wherein the optionally substituted $C_{6-10}$ aryl is an $C_{6-10}$ aryl group optionally substituted with one, two, or three members of halo, $C_{1-6}$ alkyl, $C_{1-6}$ haloalkyl, $C_{2-8}$ heterocycloalkyl, $C_{3-8}$ heteroaryl, $C_{1-6}$ alkoxy, or cyano; wherein the optionally substituted $C_{3-8}$ cycloalkyl is a $C_{3-8}$ cycloalkyl group optionally substituted with one, two, or three members of $C_{1-6}$ alkyl, $C_{1-6}$ haloalkyl, $C_{2-8}$ heterocycloalkyl, $C_{6-10}$ aryl, $C_{3-8}$ heteroaryl, $C_{1-6}$ alkoxy, halo, or hydroxyl;
$R^4$ is a six- to twelve-membered heteroaryl having at least one aromatic group and at least two heteroatoms, wherein the heteroatoms are selected from N, O, or S, wherein the heteroaryl is optionally substituted with one, two, or three members independently selected from halo, cyano, $C_{1-6}$ haloalkyl, optionally substituted $C_{1-6}$ alkyl, and —NH$_2$; wherein the optionally substituted $C_{1-6}$ alkyl is a $C_{1-6}$ alkyl group optionally substituted with one, two, or three members of hydroxyl, halo, $C_{1-6}$ alkoxy, $C_{3-8}$ cycloalkyl, $C_{2-8}$ heterocycloalkyl, $C_{6-10}$ aryl, and $C_{3-8}$ heteroaryl; and
$R^5$ is hydrogen or optionally substituted $C_{1-6}$ alkyl, wherein $R^5$ and $R^3$ together with the atoms to which they are attached optionally form a four- to eight-membered heterocyclic ring;
or a pharmaceutically acceptable salt, isomer, or a mixture thereof.
2. The compound of claim 1, wherein
n is 1 or 2;
m is 0 or 1;
each $R^1$ is independently selected from halo, $C_{1-6}$ alkyl, and $C_{1-6}$ haloalkyl;
each $R^2$ is independently selected from $C_{1-6}$ alkyl;
$R^3$ is hydrogen, $C_{1-6}$ alkyl, or $C_{3-8}$ cycloalkyl;
$R^4$ is a six- to twelve-membered heteroaryl having at least one aromatic ring and at least two nitrogen atoms, wherein the heteroaryl is optionally substituted with one, two, or three members independently selected from halo, cyano, —NH$_2$, C$_{1-6}$ haloalkyl, and C$_{1-6}$ alkyl; and R$^5$ is hydrogen, methyl, ethyl, or propyl, or R$^5$ and R$^3$ together with the atoms to which they are attached optionally form a five-membered heterocyclic ring;

or a pharmaceutically acceptable salt, isomer, or a mixture thereof.

3. The compound of claim 1, wherein each R$^1$ is independently selected from chloro, bromo, fluoro, methyl, ethyl, and propyl.

4. The compound of claim 1, wherein each R$^2$ is independently selected from methyl, ethyl, and propyl.

5. The compound of claim 1, wherein R$^3$ is hydrogen, methyl, ethyl, propyl, butyl, cyclopropyl, or cyclobutyl.

6. The compound of claim 1, wherein R$^5$ is hydrogen, methyl, ethyl, or propyl.

7. The compound of claim 1, R$^5$ and R$^3$ together with the atoms to which they are attached optionally form pyrrolidinyl.

8. The compound of claim 1, wherein R$^4$ is a monocyclic heteroaryl having at least two nitrogen atoms, wherein R$^4$ is optionally substituted with two or three members independently selected from bromo, chloro, fluoro, cyano, methyl, ethyl, propyl, fluoromethyl, difluoromethyl, trifluoromethyl, fluoroethyl, difluoroethyl, trifluoroethyl, fluoropropyl, difluoropropyl, trifluoropropyl, and —NH$_2$.

9. The compound of claim 8, wherein R$^4$ is pyrimidinyl substituted with two or three members selected from the group consisting of bromo, chloro, fluoro, cyano, methyl, ethyl, propyl, fluoromethyl, difluoromethyl, trifluoromethyl, fluoroethyl, difluoroethyl, trifluoroethyl, fluoropropyl, difluoropropyl, trifluoropropyl, and —NH$_2$.

10. The compounds of claim 1, wherein the compound is an (S)-enantiomer.

11. The compound of claim 1 wherein the compound is an (R)-enantiomer.

12. The compound of claim 1 wherein the compound is selected from the group consisting of:
 (S)-3-(5-aminopyrazin-2-yl)-5-chloro-2-(1-((2,6-diamino-5-chloropyrimidin-4-yl)amino)ethyl)-8-fluoroquinazolin-4(3H)-one;
 (S)-2,4-diamino6-((1-(3-(5-aminopyrazin-2-yl)-5-chloro-8-fluoro-4-oxo-3,4-dihydroquinazolin-2-yl)ethyl) amino)pyrimidine-5-carbonitrile;
 (S)-4-amino-6-((1-(3-(5-aminopyrazin-2-yl)-5-chloro-8-fluoro-4-oxo- 3,4-dihydroquinazoln-2yl)ethyl) amino) pyrimidine-5carbonitrile;
 (S)-2-(1-((3H-[1,2,3]triazolo[4,5-d]pyrimidin-7-yl) amino)ethyl)-3-(5-aminopyrazin-2-yl)-8-fluoroquinazolin-4(3H)-one;
 (S)-3-(5-aminopyrazin-2-yl)-5-chloro-8-fluoro-2-(1-(furo[2,3-d]pyrimidin-4-ylamino)ethyl)quinazolin-4(3H)-one;
 (S)-2,4-diamino-6-((1-(3-(5-aminopyrazin-2-yl)-5-chloro-4-oxo-3,4-dihydroquinazolin-2-yl)ethyl)amino) pyrimidine-5-carbonitrile;
 (S)-3-(5-aminopyrazin-2-yl)-5-chloro-2-(1-((2,6-diamino-5-chloropyrimidin-4-yl)amino)ethyl)quinazolin-4(3H)-one;
 (S)-3-(5-aminopyrazin-2-yl)-5-chloro-2-(cyclopropyl((2,6-diamino-5-chloropyrimidin-4-yl)amino)methyl)quinazolin-4(3H)-one;
 (S)-2,4-diamino-6-(((3-(5-aminopyrazin-2-yl)-5-chloro-4-oxo-3,4-dihydroquinazolin-2-yl)(cyclopropyl) methyl)amino)pyrimidine-5-carbonitrile;

(S)-2,4-diamino-6-(((3-(5-aminopyrazin-2-yl)-5,8-dichloro-4-oxo-3,4-dihydroquinazolin-2-yl)(cyclopropyl)methyl)amino)pyrimidine-5-carbonitrile;
 (S)-2,4-diamino-6-((1-(3-(5-aminopyrazin-2-yl)-5,8-dichloro-4-oxo-3,4-dihydroquinazolin-2-yl)ethyl)amino) pyrimidine-5-carbonitrile;
 (S)-3-(5-aminopyrazin-2-yl)-5,8-dichloro-2-(cyclopropyl ((2,6-diamino-5-chloropyrimidin-4-yl)amino)methyl) quinazolin-4(3H)-one;
 (S)-3-(5-aminopyrazin-2-yl)-5,8-dichloro-2-(1-((2,6-diamino-5-chloropyrimidin-4-yl)amino)ethyl)quinazolin-4(3H)-one;
 (S)-2-amino-4-((1-(3-(5-aminopyrazin-2-yl)-8-chloro-6-fluoro-4-oxo-3,4-dihydroquinazolin-2-yl)ethyl) amino)-6-(difluoromethyl)pyrimidine-5-carbonitrile;
 (S)-2,4-Diamino-6-((1-(3-(5-aminopyrazin-2-yl)-6,8-difluoro-4-oxo-3,4-dihydroquinazolin-2-yl)ethyl)amino) pyrimidine-5-carbonitrile;
 (S)-3-(5-Aminopyrazin-2-yl)-2-(1-((2,6-diamino-5-chloropyrimidin-4-yl)amino)ethyl)-6,8-difluoroquinazolin-4(3H)-one;
 (S)-2,4-Diamino-6-((1-(3-(5-aminopyrazin-2-yl)-8-chloro-6-fluoro-4-oxo-3,4-dihydroquinazolin-2-yl) ethyl)amino)pyrimidine-5-carbonitrile;
 (S)-3-(5-Aminopyrazin-2-yl)-8-chloro-2-(1-((2,6-diamino-5-chloropyrimidin-4-yl)amino)ethyl)-6-fluoroquinazolin-4(3H)-one;
 (S)-2-(1-((6-Amino-5-chloropyrimidin-4-yl)amino) ethyl)-3-(5-aminopyrazin-2-yl)-5-chloroquinazolin-4 (3H)-one;
 (S)-2-(((6-Amino-5-chloropyrimidin-4-yl)amino)(cyclopropyl)methyl)-3-(5-aminopyrazin-2-yl)-5,8-dichloroquinazolin-4(3H)-one; and
 (S)-2-(((6-Amino-5-chloropyrimidin-4-yl)amino)(cyclopropyl)methyl)-3-(5-aminopyrazin-2-yl)-5-chloroquinazolin-4(3H)-one;

or a pharmaceutically acceptable salt, isomer, or a mixture thereof.

13. The compound of claim 1, wherein R$^4$ is a bicyclic heteroaryl having at least two nitrogen atoms, wherein R$^4$ optionally substituted with one, two, or three members independently selected from halo, cyano, —NH$_2$, haloalkyl, and C$_{1-6}$ alkyl.

14. The compound of claim 13, wherein R$^4$ is

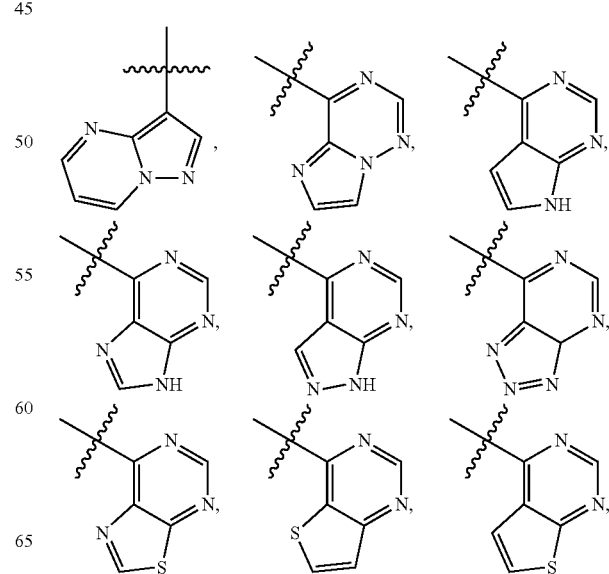

-continued

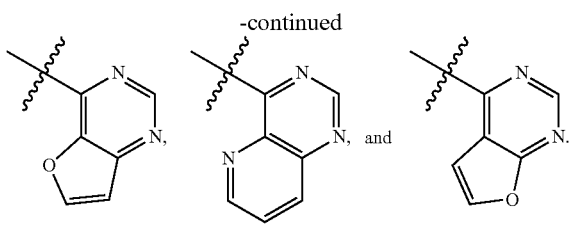

15. A pharmaceutical composition comprises the compound of claim 1 and at least one pharmaceutically acceptable vehicle.

16. A method of inhibiting the activity of phosphatidylinositol 3-kinase (P13 K), comprising administering an effective amount of a compound having the structure of formula (I):

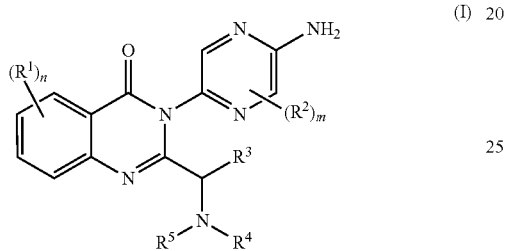

wherein:
each $R^1$ is independently selected from halo, cyano, optionally substituted $C_{1-6}$ alkyl, $C_{1-6}$ haloalkyl, $C_{1-6}$ alkoxy, optionally substituted sulfonyl, optionally substituted $C_{1-6}$ aryl, $C_{3-8}$ heteroaryl, optionally substituted $C_{3-8}$ cycloalkyl, and $C_{2-8}$ heterocycloalkyl; wherein the optionally substituted $C_{1-6}$ alkyl is a $C_{1-6}$ alkyl group optionally substituted with one, two, or three members of hydroxyl, halo, $C_{1-6}$ alkoxy, $C_{3-8}$ cycloalkyl, $C_{2-8}$ heterocycloalkyl, $C_{6-10}$ aryl, or $C_{3-8}$ heteroaryl; wherein the optionally substituted sulfonyl is a sulfonyl group optionally substituted with $C_{1-6}$ alkyl, $C_{3-8}$ cycloalkyl, $C_{2-8}$ heterocyclyl, $C_{6-10}$ aryl, or $C_{3-8}$ heteroaryl; wherein the optionally substituted $C_{6-10}$ aryl is an $C_{6-10}$ aryl group optionally substituted with one, two, or three members of halo, $C_{1-6}$ alkyl, $C_{1-6}$ haloalkyl, $C_{2-8}$ heterocycloalkyl, $C_{3-8}$ heteroaryl, $C_{1-6}$ alkoxy, or cyano; wherein the optionally substituted $C_{3-8}$ cycloalkyl is a $C_{3-8}$ cycloalkyl group optionally substituted with one, two, or three members of $C_{1-6}$ alkyl, $C_{1-6}$ haloalkyl, $C_{2-8}$ heterocycloalkyl, $C_{6-10}$ aryl, $C_{3-8}$ heteroaryl, $C_{1-6}$ alkoxy, halo, or hydroxyl;
each $R^2$ is independently selected from halo and optionally substituted $C_{1-6}$ alkyl; wherein the optionally substituted $C_{1-6}$ alkyl is a $C_{1-6}$ alkyl group optionally substituted with one, two, or three members of hydroxyl, halo, $C_{1-6}$ alkoxy, $C_{3-8}$ cycloalkyl, $C_{2-8}$ heterocycloalkyl, $C_{6-10}$ aryl, or $C_{3-8}$ heteroaryl;
$R^3$ is hydrogen, optionally substituted $C_{1-6}$ alkyl, optionally substituted $C_{6-10}$ aryl, or optionally substituted $C_{3-8}$ cycloalkyl; wherein the optionally substituted $C_{1-6}$ alkyl is a $C_{1-6}$ alkyl group optionally substituted with one, two, or three members of hydroxyl, halo, $C_{1-6}$ alkoxy, $C_{3-8}$ cycloalkyl, $C_{2-8}$ heterocycloalkyl, $C_{6-10}$ aryl, or $C_{3-8}$ heteroaryl; wherein the optionally substituted $C_{6-10}$ aryl is an $C_{6-10}$ aryl group optionally substituted with one, two, or three members of halo, $C_{1-6}$ alkyl, $C_{1-6}$ haloalkyl, $C_{2-8}$ heterocycloalkyl, $C_{3-8}$ heteroaryl, $C_{1-6}$ alkoxy, or cyano; wherein the optionally substituted $C_{3-8}$ cycloalkyl is a $C_{3-8}$ cycloalkyl group optionally substituted with one, two, or three members of $C_{1-6}$ alkyl, $C_{1-6}$ haloalkyl, $C_{2-8}$ heterocycloalkyl, $C_{6-10}$ aryl, $C_{3-8}$ heteroaryl, $C_{1-6}$ alkoxy, halo, or hydroxyl;
$R^4$ is a six- to twelve-membered heteroaryl having at least one aromatic group and at least two heteroatoms, wherein the heteroatoms are selected from N, O, or S, wherein the heteroaryl is optionally substituted with one, two, or three members independently selected from halo, cyano, $C_{1-6}$ haloalkyl, optionally substituted $C_{1-6}$ alkyl, and —$NH_2$; wherein the optionally substituted $C_{1-6}$ alkyl is a $C_{1-6}$ alkyl group optionally substituted with one, two, or three members of hydroxyl, halo, $C_{1-6}$ alkoxy, $C_{3-8}$ cycloalkyl, $C_{2-8}$ heterocycloalkyl, $C_{6-10}$ aryl, and $C_{3-8}$ heteroaryl; and
$R^5$ is hydrogen or optionally substituted $C_{1-6}$ alkyl, wherein $R^5$ and $R^3$ together with the atoms to which they are attached optionally form a four- to eight-membered heterocyclic ring;
or a pharmaceutically acceptable salt, isomer, or a mixture thereof.

17. The method of claim 16 wherein
n is 1 or 2;
m is 0 or 2;
each $R^1$ is independently selected from halo, $C_{1-6}$ alkyl, and $C_{1-6}$ haloalkyl;
each $R^2$ is independently selected from $C_{1-6}$ alkyl;
$R^3$ is hydrogen, $C_{1-6}$ alkyl, or $C^{3-8}$ cycloalkyl;
$R^4$ is a six- to twelve-membered heteroaryl having at least one aromatic ring and at least two nitrogen atoms, and wherein the heteroaryl is optionally substituted with one, two, or three members independently selected from halo, cyano, —$NH_2$, $C_{1-6}$ haloalkyl, and $C_{1-¬}$alkyl; and
$R^5$ is hydrogen, methyl, ethyl, or propyl, or $R^5$ and $R^3$ together with the atoms to which they are attached optionally form a five-membered heterocyclic ring;
or a pharmaceutically acceptable salt, isomer, or a mixture thereof.

18. The method of claim 16, wherein each $R^1$ is independently selected from chloro, bromo, fluoro, methyl, ethyl, and propyl.

19. The method of claim 16, wherein each $R^2$ is independently selected from methyl, ethyl, and propyl.

20. The method of claim 16, wherein $R^3$ is hydrogen, ethyl, ethyl, propyl, butyl, cyclopropyl, or cyclobutyl.

21. The method of claim 16, wherein $R^5$ is hydrogen, methyl, ethyl, or propyl.

22. The method of claim 16, $R^5$ and $R^3$ together with the atoms to which they are attached optionally form pyrrolidinyl.

23. The method of claim 16, wherein $R^4$ is a monocyclic heteroaryl having at least two nitrogen atoms, wherein $R^4$ is optionally substituted with two or three members independently selected from bromo, chloro, fluoro, cyano, methyl, ethyl, propyl, fluoromethyl, difluoromethyl, trifluoromethyl, fluoroethyl, difluoroethyl, trifluoroethyl, fluoropropyl, difluoropropyl, trifluoropropyl, and —$NH_2$.

24. The method of claim 23, wherein $R^4$ is pyrimidinyl substituted with two or three members selected from the group consisting of bromo, chloro, fluoro, cyano, methyl, ethyl, propyl, fluommethyl, difluoromethyl, trifluoromethyl, fluoroethyl, difluoroethyl, trifluoroethyl, fiuoropropyl, difluoropropyl, trifluoropropyl, and —$NH_2$.

25. The method of claim 16, wherein $R^4$ is a bicyclic heteroaryl having at least two nitrogen atoms, wherein $R^4$ is optionally substituted with one, two, or three members independently selected from halo, cyano, —NH$_2$, haloalkyl, and $C_{1-6}$ alkyl.

26. The method of claim 25, wherein $R^4$ is

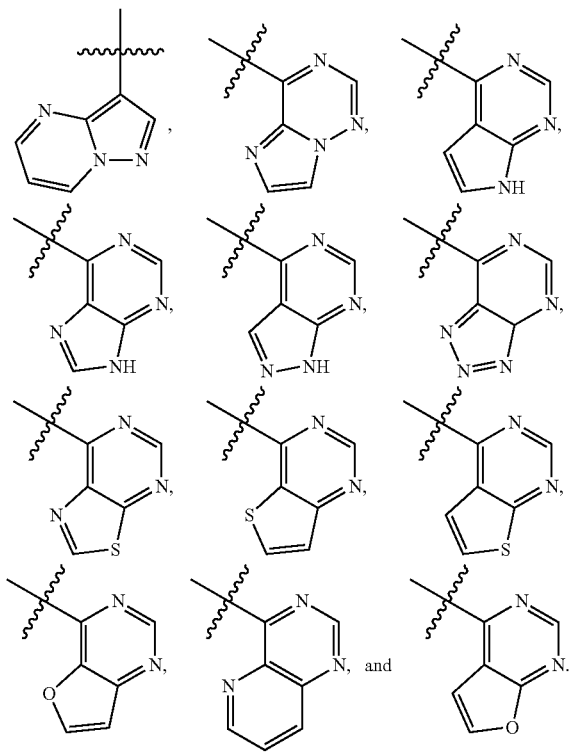

27. The method of claim 16, wherein the PI3K is PI3k-β and PI3Kδ.

28. The method of claim 16, wherein the compound is presented in a pharmaceutical composition.

29. The method of claim 16, wherein the compound is selected from the group consisting of:

(S)-3-(5-aminopyrazin-2-yl)-5-chloro-2-(1-((2,6-diamino-5-chloropyrimidin-4-yl)amino)ethyl)-8-fluoro-quinazolin-4(3H) )-one;

(S)-2,4-diamino-6-((1-(3-(5-aminopyrazin-2-yl)-5-chloro-8-fluoro-4-oxo-3,4-dihydroquinazolin-2-yl)ethyl)amino)pyrimidine-5-carbonitrile;

(S)-4-amino-6-((1-(3-(5-aminopyrazin-2-yl)-5-chloro-8-fluoro-4-oxo-3,4-dihydroquinazolin-2-yl)ethyl)amino)pyrimidine-5-carbonitrile;

(S)-2-(1-((3H-[1,2,3]thiazolo[4,5-d]pyrimidin-7-yl)amino)ethyl)-3-(5-aminopyrazin-2-yl)-8-fluoroquinazolin-4(3H)-one;

(S)-3-(5-aminopyrazin-2-yl)-5-chloro-8-fluoro-2-(1-(furo[2,3-d]pyrimidin-4-ylamino)ethyl)quinazolin-4(3H)-one;

(S)-2,4-diamino-6-((1-(3-(5-aminopyrazin-2-yl)-5-chloro-4-oxo-3,4-dihydroquinazolin-2-yl)ethyl)amino)pyrimidine-5-carbonitrile;

(S)-3-(5-aminopyrazin-2yl)-5-chloro-2-(1-((2,6 -diamino-5-chloropyrimidin-4-yl)amino)ethyl)quinazolin-4(3H)-one;

(S)-3-(5-aminopyrazin-2-yl)-5-chloro-2-(cyclopropyl((2,6-diamino-5-chloropyrirnidin-4-yl)amino)methyl)quinazolin-4-(3H)-one;

(S)-2,4-diamino-6-(((3-(5-aminopyrazin-2-yl)-5-chloro-4-oxo-3,4-dihydroquinazolin-2-yl)cyclopropyl)methyl)amino)pyrimidine-5-carbonitrile;

(S)-2,4-diamino-6-(((3-(5-aminopyrazin-2-yl)-5,8-dichloro -4-oxo-3,4-dihydroquinazolin-2-yl)(cyclopropyl)methyl)amino)pyrimidine-5-carbonitrile;

(S)-2,4-diamino-6-((1-(3-(5-aminopyrazin-2-yl)-5,8-dichloro-4-oxo-3,4-dihydroquinazolin-2-yl)ethyl)amino)pyrimidine-5-carbonitrile;

(S)-3-(5-aminopyrazin-2yl)-5,8-dichloro-2-(cyclopropyl((2,6-diamino-5-chloropyrimidin-4-yl)amino)methyl)quinazolin-4(3H)one;

(S)-3-(5-aminopyrazin-2-yl)-5,8-dichloro 2-(1-((2,6-diamino-5-chloropyrimidin-4-yl)amino)ethyl)quinazolin-4(3H)-one;

(S)-2-amino-4-((1 -(3-(5-aminopyrazin-2yl))-8-chloro-6-fluoro-4-oxo-3,4-dihydroquinazolin-2-yl)ethyl)amino)-6-(difluoromethyl)pyrimidine-5-carbonitrile;

(S)-2,4-Diamino-6-((1-(3-(5-aminopyrazin-2-yl)-6,8- difluoro-4-oxo-3,4-dihydroquinazolin-2-yl)ethyl)amino)pyrimidine-5-carbonitrile;

(S)-3-(5-Aminopyrazin-2-yl)-2-(1((,2,6-diamino-5-chloropyrimidin-4-yl)amino)ethyl)-6,8-difluoroquinazolin-4(3H)-one;

(S)-2,4-Diamino-6-((1-(3-(5-aminopyrazin-2-yl)-8-chloro-6-fluoro-4-oxo-3,4-dihydroquinazolin-2-yl)ethyl)amino)pyrimidine-5-carbonitrile;

(S)-3-(5-Aminopyrazin-2-yl)-8-chloro-2-(1-((2,6-diamino-5-chloropyrimidin-4-yl)amino)ethyly)-6-fluoroquinazolin-4(3H)-one;

(S)-2-(1 ((6-Amino-5-chloropyrimidin-4-yl)amino)ethyl)-3-(5aminopyrazin-2-yl)-5-chloroquinazolin-4 (3H)-one;

(S)-2-(((6-Amino-5-chloropyrimidin-4-yl)amino)(cyclopropyl)methyl)-3-(5-aminopyrazin-2-yl)-5,8-dichloroduinazolin-4(3H)-one; and (S)-2-(((6-Amino-5-chloropyrimidin-4-yl)amino)(cyclopropyl)methyl)-3-(5-aminopyrazin-2-yl)-5-chloroquinazolin-4(3H)-one;

or a pharmaceutically acceptable salt, isomer, or a mixture thereof.

30. The method of claim 29, wherein the PI3K is PI3K-β and PI3Kδ.

31. The method of claim 29, wherein the compound is presented in a pharmaceutical composition.

32. A kit comprises the compound of claim 1 or a label and/or instructions for use.

\* \* \* \* \*

UNITED STATES PATENT AND TRADEMARK OFFICE
CERTIFICATE OF CORRECTION

| | |
|---|---|
| PATENT NO. | : 9,499,523 B2 |
| APPLICATION NO. | : 14/736025 |
| DATED | : November 22, 2016 |
| INVENTOR(S) | : Musong Kim et al. |

It is certified that error appears in the above-identified patent and that said Letters Patent is hereby corrected as shown below:

In the Specification

At Column 23, Line 40, "14" should be replaced with – "16"

At Column 24, Line 9, "16" should be replaced with – "18"

At Column 24, Line 39, "18" should be replaced with – "19"

At Column 24, Line 53, "19" should be replaced with – "20"

At Column 25, Line 6, "20" should be replaced with – "21"

At Column 25, Line 18, "21" should be replaced with – "14"

Signed and Sealed this
Twelfth Day of September, 2017

Joseph Matal
*Performing the Functions and Duties of the
Under Secretary of Commerce for Intellectual Property and
Director of the United States Patent and Trademark Office*